(12) United States Patent
Wittmershaus et al.

(10) Patent No.: US 11,854,675 B1
(45) Date of Patent: Dec. 26, 2023

(54) MACHINE LEARNING EXTRACTION OF CLINICAL VARIABLE VALUES FOR SUBJECTS FROM CLINICAL RECORD DATA

(71) Applicant: Flatiron Health, Inc., New York, NY (US)

(72) Inventors: Brett Wittmershaus, Brooklyn, NY (US); Guy Amster, Hoboken, NJ (US); Michael Waskom, New York, NY (US); Natalie Roher, New York, NY (US); Nisha Singh, Queens, NY (US); Sharang Phadke, New York, NY (US); Will Shapiro, New York, NY (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 17/963,998

(22) Filed: Oct. 11, 2022

(51) Int. Cl.
  *G16H 10/60* (2018.01)
  *G06F 16/35* (2019.01)
  *G06N 20/00* (2019.01)

(52) U.S. Cl.
  CPC ............ *G16H 10/60* (2018.01); *G06F 16/35* (2019.01); *G06N 20/00* (2019.01)

(58) Field of Classification Search
  CPC ... G06F 1/00–2221/2153; G16H 10/00–80/00; G06N 3/00–99/007
  See application file for complete search history.

(56) References Cited

U.S. PATENT DOCUMENTS

| | | | |
|---|---|---|---|
| 10,395,772 B1 * | 8/2019 | Lucas | G06F 18/217 |
| 2003/0154108 A1 | 8/2003 | Fletcher-Haynes et al. | |
| 2004/0010758 A1 * | 1/2004 | Sarkar | G06V 30/12 |
| | | | 715/256 |
| 2008/0086433 A1 * | 4/2008 | Schmidtler | G06N 20/10 |
| | | | 707/E17.09 |
| 2009/0082640 A1 | 3/2009 | Kovach et al. | |
| 2013/0224117 A1 * | 8/2013 | Royall | G16H 50/50 |
| | | | 424/9.2 |
| 2014/0279721 A1 | 9/2014 | Siegel et al. | |
| 2014/0324463 A1 | 10/2014 | Buck et al. | |

(Continued)

OTHER PUBLICATIONS

Solares et al., "Deep learning for electronic health records: A comparative review of multiple deep neural architectures," Journal of Biomedical Informatics 101 (2020) 103337; https://doi.org/10.1016/j.jbi.2019.103337. (Year: 2020).*

(Continued)

*Primary Examiner* — Jonathon A. Szumny
(74) *Attorney, Agent, or Firm* — Wolf, Greenfield & Sacks, P.C.

(57) ABSTRACT

Described herein are techniques of using machine learning to automatically extract clinical variable values for subjects from clinical record data. The techniques designate certain clinical variables as hybrid variables that can be assigned values by machine learning model prediction. The techniques process, using a machine learning model trained to predict a value of a hybrid variable, clinical record data associated with a subject to obtain a predicted hybrid variable value and an associated confidence score. The techniques set the value of the hybrid variable for the subject to the predicted hybrid variable value when the model prediction is of sufficiently high confidence.

20 Claims, 16 Drawing Sheets

(56) References Cited

U.S. PATENT DOCUMENTS

| | | | |
|---|---|---|---|
| 2016/0188835 A1 | 6/2016 | Devaux et al. | |
| 2017/0185893 A1* | 6/2017 | Wetta | G16H 40/20 |
| 2018/0046764 A1 | 2/2018 | Katwala et al. | |
| 2018/0349560 A1 | 12/2018 | McCloskey et al. | |
| 2018/0373941 A1* | 12/2018 | Kwant | G08G 1/0145 |
| 2019/0007354 A1 | 1/2019 | Bulut et al. | |
| 2019/0259058 A1 | 8/2019 | Chakraborty | |
| 2020/0273570 A1* | 8/2020 | Subramanian | G06N 20/00 |
| 2021/0027894 A1 | 1/2021 | Rich et al. | |
| 2021/0035015 A1* | 2/2021 | Edgar | G06F 18/211 |
| 2021/0255880 A1 | 8/2021 | Markson et al. | |
| 2021/0257106 A1 | 8/2021 | Birnbaum et al. | |
| 2021/0391087 A1 | 12/2021 | Gippetti et al. | |
| 2022/0036137 A1* | 2/2022 | Muselli | G06F 18/2178 |
| 2022/0108073 A1* | 4/2022 | Menon | G06F 18/2193 |
| 2022/0122736 A1* | 4/2022 | Godden | G06N 3/086 |
| 2022/0246257 A1 | 8/2022 | Priestas et al. | |
| 2022/0327404 A1* | 10/2022 | Godden | G06N 20/00 |
| 2023/0195847 A1* | 6/2023 | Koukoumidis | G06F 18/285 |
| | | | 704/9 |

OTHER PUBLICATIONS

Rajkomar et al., "Scalable and accurate deep learning with electronic health records," npj Digital Medicine (2018) 1:18; doi:10.1038/s41746-018-0029-1. (Year: 2018).*

* cited by examiner

300

| Patient ID | Stage | Metastatic diagnosis | Metastatic diagnosis date |
|---|---|---|---|
| P001 | IIA | No | |
| P002 | *IVB* | *Yes* | *2018-05-10* |
| P003 | *IIIC* | *Yes* | 2019-03-12 |
| P004 | *II* | No | |
| P004 | IVA | Yes | 2016-01-20 |

| Human-extracted | *ML-extracted* |
|---|---|

FIG. 3

MACHINE LEARNING EXTRACTION OF CLINICAL VARIABLE VALUES FOR SUBJECTS FROM CLINICAL RECORD DATA

BACKGROUND

Real-world data (RWD) is clinical record data associated with subjects (e.g., patients). The data may include information about a subject's health (e.g., diagnosed illness, stage of illness, age, weight, height, allergies, date of birth, and/or other information) and delivery of healthcare (e.g., prescribed drugs, medical test history, medical image data, and/or other information). RWD can come from various sources including electronic health records (EHRs), insurance claims, monitoring devices (e.g., wearable devices, at home monitoring devices), mobile devices, and/or other sources.

RWD allows researchers to go beyond data gathered through a controlled trial. Data from controlled trials is limited to the characteristics of a cohort examined in a trial. Moreover, obtaining data through controlled trials requires significant investment and time. By contrast, RWD can be collected from any number of groups. Insights gained from the data can be valuable for use in medical diagnosis, medical treatment, development of treatments (e.g., procedures, drugs, and/or other types of treatments), life science research, and/or other purposes.

SUMMARY

Described herein are techniques that enable use of machine learning to automate extraction of information (RWD) about subjects from clinical record data. The techniques employ a hybrid approach in which certain clinical variable values can be assigned manually or by prediction of a machine learning model. The techniques intelligently decide between using a machine learning model prediction versus requiring manual extraction based on whether the machine learning model prediction meets a threshold level of confidence. The techniques significantly increase throughput of information extraction from clinical record data without affecting quality (e.g., accuracy) of the extracted information. For example, in some cases, the techniques may increase the amount of data on which extraction can be performed in a period of time by 400%.

According to some embodiments, a method of using machine learning to automatically extract values of clinical variables for a plurality of subjects from clinical record data. The clinical variables include hybrid variables that can have their values assigned by machine learning model prediction or by manual extraction. The method comprises: obtaining clinical record data associated with a first subject of the plurality of subjects; processing, using a first machine learning model trained to predict a value of a first hybrid variable, the clinical record data associated with the first subject to obtain a predicted first hybrid variable value and an associated confidence score; determining, using the confidence score associated with the predicted first hybrid variable value, whether to set a first hybrid variable value for the first subject to the predicted first hybrid variable value; in response to determining to set the first hybrid variable value for the first subject to the predicted first hybrid variable value: setting the first hybrid variable value for the first subject to the predicted first hybrid variable value in a dataset comprising clinical variable values for the plurality of subjects; and in response to determining to not set the first hybrid variable value for the first subject to the predicted first hybrid variable value: obtaining input indicating a manually extracted first hybrid variable value for the first subject; and setting the first hybrid variable value for the first subject to the manually extracted first hybrid variable value in the dataset comprising clinical variable values for the plurality of subjects.

In some embodiments, obtaining the input indicating the manually extracted first hybrid variable value for the first subject comprises: generating a request for the manually extracted first hybrid variable value for the first subject; and receiving, in response to the request, the input indicating the manually extracted first hybrid variable value for the first subject. In some embodiments, the clinical record data comprises unstructured textual data, and processing the clinical record data associated with the first subject comprises: identifying at least one portion of the unstructured textual data associated with the first hybrid variable; generating, using the at least one portion of the unstructured textual data associated with the first hybrid variable, at least one set of features; and providing the at least one set of features as input to the first machine learning model to obtain an output indicating the predicted first hybrid variable value and the confidence score associated with the predicted first hybrid variable value. In some embodiments, the first machine learning model is trained to output probability values for each of multiple output classes, and the confidence score associated with the predicted first hybrid variable value is a probability value output for a respective one of the multiple output classes.

In some embodiments, determining, using the confidence score associated with the predicted first hybrid variable value, whether to set the value of the first hybrid variable value for the first subject to the predicted first hybrid variable value comprises: determining whether the confidence score associated with the predicted first hybrid variable value meets a threshold confidence score; determining to set the first hybrid variable value for the first subject to the predicted first hybrid variable value when it is determined that the confidence score associated with the predicted first hybrid variable value meets the threshold confidence score; and determining to not set the first hybrid variable value for the first subject to the predicted first hybrid variable value when it is determined that the confidence score associated with the predicted first hybrid variable value does not meet the threshold confidence score. In some embodiments, the threshold confidence score is determined by: identifying a plurality of candidate threshold confidence scores; for each one of the plurality of candidate threshold confidence scores: processing clinical record data associated with a set of subjects using the first machine learning model to obtain a set of predicted first hybrid variable values and a corresponding set of confidence scores; determining a set of first hybrid variable values for the set of subjects using the candidate threshold confidence score; determining a measure of quality for the set of first hybrid variable values determined using the candidate threshold confidence score; and selecting the threshold confidence score from the plurality of candidate threshold confidence scores based on measures of quality determined for the plurality of candidate threshold scores.

In some embodiments, the hybrid variable is a stage of cancer of the subject. In some embodiments, the hybrid variable is a metastatic cancer diagnosis of the subject. In some embodiments, the hybrid variable is a date of metastatic cancer diagnosis of the subject. In some embodiments, the clinical variables include a non-hybrid variable that cannot have its value assigned by machine learning model prediction, and the method further comprises: obtaining input indicating a manually extracted value of the non-hybrid variable for the first subject; and setting the non-hybrid variable value for the first subject to the manually extracted value.

In some embodiments, the method further comprises: processing, using a second machine learning model trained to predict a value of a second hybrid variable, the clinical record data associated with the first subject to obtain a predicted second hybrid variable value and an associated second confidence score; determining, using the second confidence score associated with the predicted second hybrid variable value, whether to set a second hybrid variable value for the first subject to the predicted second hybrid variable value; in response to determining to set the second hybrid variable value for the first subject to the predicted second hybrid variable value: setting the second hybrid variable value for the first subject to the predicted second hybrid variable value in the dataset comprising clinical variable values for the plurality of subjects; and in response to not determining to set the second hybrid variable value for the first subject to the predicted second hybrid variable value: obtaining, through a graphical user interface (GUI), user input indicating a manually extracted second hybrid variable value for the first subject; and setting the second hybrid variable value for the first subject to the manually extracted second hybrid variable value in the dataset comprising clinical variable values for the plurality of subjects.

According to some embodiments, a system for using machine learning to automatically extract values of clinical variables for a plurality of subjects from clinical record data, the clinical variables including hybrid variables that can have their values assigned by machine learning model prediction or by manual extraction. The system comprises: at least one processor; and at least one non-transitory computer-readable storage medium storing instructions that, when executed by the at least one processor, cause the at least one processor to perform: obtaining clinical record data associated with a first subject of the plurality of subjects; processing, using a first machine learning model trained to predict a value of a first hybrid variable, the clinical record data associated with the first subject to obtain a predicted first hybrid variable value and an associated confidence score; determining, using the confidence score associated with the predicted first hybrid variable value, whether to set a first hybrid variable value for the first subject to the predicted first hybrid variable value; in response to determining to set the first hybrid variable value for the first subject to the predicted first hybrid variable value: setting the first hybrid variable value for the first subject to the predicted first hybrid variable value in a dataset comprising clinical variable values for the plurality of subjects; and in response to determining to not set the first hybrid variable value for the first subject to the predicted first hybrid variable value: obtaining input indicating a manually extracted first hybrid variable value for the first subject; and setting the first hybrid variable value for the first subject to the manually extracted first hybrid variable value in the dataset comprising clinical variable values for the plurality of subjects.

In some embodiments, obtaining the input indicating the manually extracted first hybrid variable value for the first subject comprises: generating a request for the manually extracted first hybrid variable value for the first subject; and receiving, in response to the request, the input indicating the manually extracted first hybrid variable value for the first subject.

In some embodiments, the clinical record data comprises unstructured textual data, and processing the clinical record data associated with the first subject comprises: identifying at least one portion of the unstructured textual data associated with the first hybrid variable; generating, using the at least one portion of the unstructured textual data associated with the first hybrid variable, at least one set of features; and providing the at least one set of features as input to the first machine learning model to obtain an output indicating the predicted first hybrid variable value and the confidence score associated with the predicted first hybrid variable value.

In some embodiments, the first machine learning model is trained to output probability values for each of multiple output classes, and the confidence score associated with the predicted first hybrid variable value is a probability value output for a respective one of the multiple output classes. In some embodiments, determining, using the confidence score associated with the predicted first hybrid variable value, whether to set the value of the first hybrid variable value for the first subject to the predicted first hybrid variable value comprises: determining whether the confidence score associated with the predicted first hybrid variable value meets a threshold confidence score; determining to set the first hybrid variable value for the first subject to the predicted first hybrid variable value when it is determined that the confidence score associated with the predicted first hybrid variable value meets the threshold confidence score; and determining to not set the first hybrid variable value for the first subject to the predicted first hybrid variable value when it is determined that the confidence score associated with the predicted first hybrid variable value does not meet the threshold confidence score.

In some embodiments, the clinical variables include a non-hybrid variable that cannot have its value assigned by machine learning model prediction, and the method further comprises: obtaining input indicating a manually extracted non-hybrid variable value for the first subject; and setting the non-hybrid variable value for the first subject to the manually extracted non-hybrid variable value.

According to some embodiments, at least one non-transitory computer-readable storage medium storing instructions is provided. The instructions, when executed by at least one processor, cause the at least one processor to perform a method of using machine learning to automatically extract values of clinical variables for a plurality of subjects from clinical record data, the clinical variables including hybrid variables that can have their values assigned by machine learning model prediction or by manual extraction. The method comprises: obtaining clinical record data associated with a first subject of the plurality of subjects; processing, using a first machine learning model trained to predict a value of a first hybrid variable, the clinical record data associated with the first subject to obtain a predicted first hybrid variable value and an associated confidence score; determining, using the confidence score associated with the predicted first hybrid variable value, whether to set a first hybrid variable value for the first subject to the predicted first hybrid variable value; in response to determining to set the first hybrid variable value for the first subject to the predicted first hybrid variable value: setting the first hybrid variable value for the first subject to the predicted first hybrid variable value in a dataset comprising clinical variable values for the plurality of subjects; and in response to determining to not set the first hybrid variable value for the first subject to the predicted first hybrid variable value: obtaining input indicating a manually extracted first hybrid variable value for the first subject; and setting the first hybrid variable value for the first subject to the manually extracted first hybrid variable value in the dataset comprising clinical variable values for the plurality of subjects.

In some embodiments, the first machine learning model is trained to output probability values for each of multiple output classes, and the confidence score associated with the predicted first hybrid variable value is a probability value output for a respective one of the multiple output classes. In some embodiments, determining, using the confidence score associated with the predicted first hybrid variable value, whether to set the value of the first hybrid variable value for the first subject to the predicted first hybrid variable value comprises: determining whether the confidence score associated with the predicted first hybrid variable value meets a threshold confidence score; determining to set the first hybrid variable value for the first subject to the predicted first hybrid variable value when it is determined that the confidence score associated with the predicted first hybrid variable value meets the threshold confidence score; and determining to not set the first hybrid variable value for the first subject to the predicted first hybrid variable value when it is determined that the confidence score associated with the predicted first hybrid variable value does not meet the threshold confidence score.

According to some embodiments, a method of using machine learning to configure a graphical user interface (GUI) through which a user can provide input indicating values of clinical variables extracted from clinical record data for a plurality of subjects is provided. The clinical variables include hybrid variables that can have their values assigned by machine learning prediction or manual extraction. The method comprises: using at least one processor to perform: obtaining clinical record data associated with a subject; processing, using a machine learning model, the clinical record data associated with the subject to obtain a predicted hybrid variable value and a confidence score associated with the predicted hybrid variable value; determining, using the confidence score associated with the predicted hybrid variable value, whether to set a hybrid variable value for the subject to the predicted hybrid variable value; generating a GUI portion presenting the predicted hybrid variable value as the hybrid variable value for the subject when it is determined to set the hybrid variable value for the subject to the predicted hybrid variable value, the generating comprising: configuring the GUI portion to restrict user modification of the hybrid variable value for the subject through the GUI.

In some embodiments, configuring the portion of the GUI to restrict user modification of the hybrid variable value for the subject through the GUI comprises: removing, from the GUI portion, an interface for modification of the hybrid variable value for the subject. In some embodiments, configuring the portion of the GUI to restrict user modification of the hybrid variable value for the subject through the GUI comprises configuring the GUI to: detect user input to modify the hybrid variable value for the subject; and generate a graphical element requesting user input confirming that the predicted hybrid variable value is to be overridden in response to detecting the user input to modify the hybrid variable value for the subject. In some embodiments, generating the graphical element requesting user input confirming that the predicted hybrid variable value is to be overridden in response to detecting the user input to modify the hybrid variable value for the subject comprises: generating an overlaid dialogue box that provides a first option to discard a modification of the hybrid variable value for the subject and a second option to submit the modification of the hybrid variable value for the subject.

In some embodiments, configuring the GUI portion to restrict user modification of the hybrid variable value for the subject through the GUI comprises: preventing entry of user input in an interface for modification of the hybrid variable value for the subject. In some embodiments, generating the GUI portion further comprises: configuring the GUI portion to indicate that the hybrid variable value for the subject is machine learning model predicted. In some embodiments, configuring the GUI portion to indicate that the hybrid variable value for the subject is machine learning model predicted: displaying, in the GUI portion, text indicating that the hybrid variable value presented in the GUI portion is generated by machine learning model prediction. In some embodiments, configuring the GUI portion to indicate that the hybrid variable value for the subject is machine learning model predicted comprises configuring the GUI portion to: detect a particular action within the GUI portion; and display a message indicating that the hybrid variable value for the subject is machine learning model predicted in response to detecting the particular action within the GUI portion.

In some embodiments, the method further comprises: generating a GUI portion through which a user can provide input indicating the hybrid variable value for the first subject when it is determined to not set the hybrid variable value for the first subject to the predicted hybrid variable value, the generating comprising: configuring the GUI portion to receive user input indicating a value of the hybrid variable for the first subject through the GUI.

According to some embodiments, a system is provided. The system uses machine learning to configure a GUI through which a user can provide input indicating values of clinical variables extracted from clinical record data for a plurality of subjects. The clinical variables include hybrid variables that can have their values assigned by machine learning model prediction or manual extraction. The system comprises: at least one processor; and at least one non-transitory computer-readable storage medium storing instructions that, when executed by the at least one processor, cause the at least one processor to: obtain clinical record data associated with a subject; process, using a machine learning model, the clinical record data associated with the subject to obtain a predicted hybrid variable value and a confidence score associated with the predicted hybrid variable value; determine, using the confidence score associated with the predicted hybrid variable value, whether to set a hybrid variable value for the subject to the predicted hybrid variable value; generate a GUI portion presenting the predicted hybrid variable value as the hybrid variable value for the subject when it is determined to set the hybrid variable value for the subject to the predicted hybrid variable value, the generating comprising: configuring the GUI portion to restrict user modification of the hybrid variable value for the subject through the GUI.

In some embodiments, configuring the portion of the GUI to restrict user modification of the hybrid variable value for the subject through the GUI comprises: removing, from the GUI portion, an interface for modification of the hybrid variable value for the subject. In some embodiments, configuring the portion of the GUI to restrict user modification of the hybrid variable value for the subject through the GUI comprises configuring the GUI to: detect user input to modify the hybrid variable value for the subject; and generate a graphical element requesting user input confirming that the predicted hybrid variable value is to be overridden in response to detecting the user input to modify the hybrid variable value for the subject. In some embodiments, generating the graphical element requesting user input confirming that the predicted hybrid variable value is to be overridden in response to detecting the user input to modify the hybrid variable value for the subject comprises: generating a dialogue box that provides a first option to discard a modification of the hybrid variable value for the subject and a second option to submit the modification of the hybrid variable value for the subject.

In some embodiments, configuring the GUI portion to restrict user modification of the hybrid variable value for the subject through the GUI comprises: preventing entry of user input in a GUI portion for modification of the hybrid variable value for the subject. In some embodiments, generating the GUI portion further comprises: configuring the GUI portion to indicate that the hybrid variable value for the subject is machine learning model predicted. In some embodiments, configuring the GUI portion to indicate that the hybrid variable value for the subject is machine learning model predicted comprises: displaying, in the GUI portion, text indicating that the hybrid variable value presented in the GUI portion is generated by machine learning model prediction. In some embodiments, configuring the GUI portion to indicate that the hybrid variable value for the subject is machine learning model predicted comprises configuring the GUI portion to: detect a particular action within the GUI portion; and display a message indicating that the hybrid variable value for the subject is machine learning model predicted in response to detecting the particular action within the GUI portion.

In some embodiments, the instructions further cause the at least one processor to generate a GUI portion through which a user can provide input indicating the hybrid variable value for the subject when it is determined to not set the hybrid variable value for the subject to the predicted hybrid variable value, the generating comprising: configuring the GUI portion to receive user input indicating a manually extracted value of the hybrid variable for the subject through the GUI.

According to some embodiments, at least one non-transitory computer-readable storage medium storing instructions is provided. The instructions, when executed by at least one processor, cause the at least one processor to perform a method of using machine learning to configure a graphical user interface (GUI) through which a user can provide input indicating values of clinical variables extracted from clinical record data for a plurality of subjects. The clinical variables include hybrid variables that can have their values assigned by machine learning prediction or manual extraction. The method comprises: obtaining clinical record data associated with a subject; processing, using a machine learning model, the clinical record data associated with the subject to obtain a predicted hybrid variable value and a confidence score associated with the predicted hybrid variable value; determining, using the confidence score associated with the predicted hybrid variable value, whether to set a hybrid variable value for the subject to the predicted hybrid variable value; generating a GUI portion presenting the predicted hybrid variable value as the hybrid variable value for the subject when it is determined to set the hybrid variable value for the subject to the predicted hybrid variable value, the generating comprising: configuring the GUI portion to restrict user modification of the hybrid variable value for the subject through the GUI.

In some embodiments, configuring the portion of the GUI to restrict user modification of the hybrid variable value for the subject through the GUI comprises: removing, from the GUI portion, an interface for modification of the hybrid variable value for the subject. In some embodiments, configuring the portion of the GUI to restrict user modification of the hybrid variable value for the subject through the GUI comprises configuring the GUI to: detect user input to modify the hybrid variable value for the subject; and generate a graphical element requesting user input confirming that the predicted hybrid variable value is to be overridden in response to detecting the user input to modify the hybrid variable value for the subject. In some embodiments, generating the GUI portion further comprises: configuring the GUI portion to indicate that the hybrid variable value for the subject is machine learning model predicted.

The foregoing is a non-limiting summary.

BRIEF DESCRIPTION OF DRAWINGS

Various aspects and embodiments will be described with reference to the following figures. It should be appreciated that the figures are not necessarily drawn to scale. Items appearing in multiple figures are indicated by the same or a similar reference number in all the figures in which they appear.

FIG. 3 is a portion of an example dataset of extracted clinical variable values for multiple subjects, according to some embodiments of the technology described herein.

DETAILED DESCRIPTION

Figure 1A:
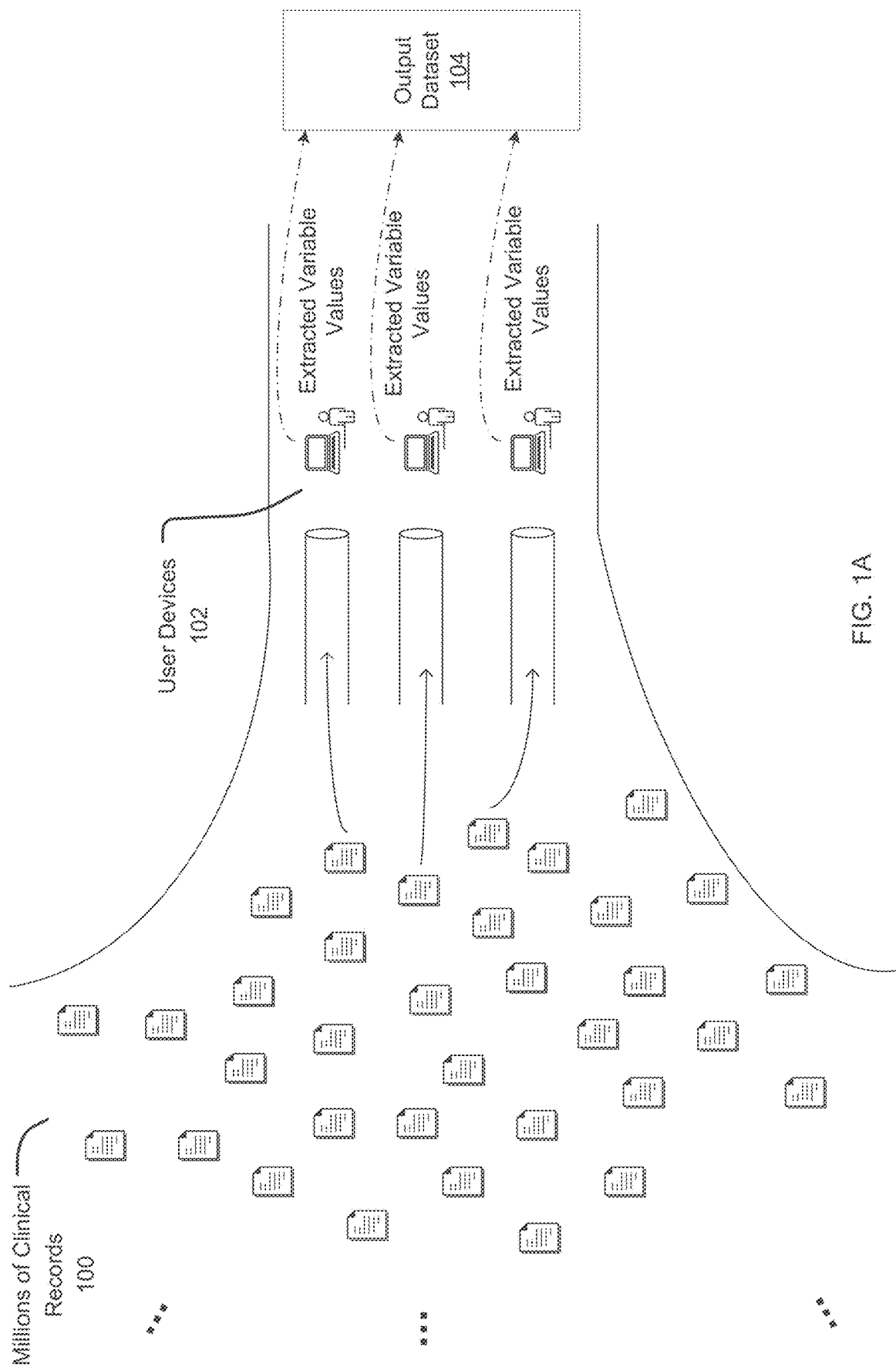
FIG. 1A illustrates manual extraction of clinical variable values from clinical record data.

The inventors have developed techniques of using machine learning to automatically extract clinical variable values for subjects from clinical record data. The techniques designate certain clinical variables as hybrid variables that can have their values assigned by machine learning model prediction or by manual extraction (e.g., by a trained expert). Examples of clinical variables include type of cancer, stage of cancer diagnosis, whether there is metastatic diagnosis, date of metastatic diagnosis, prognosis, identification of prescribed drugs, and/or other variables.

Healthcare organizations such as medical facilities (e.g., hospitals and clinics), pharmaceutical companies, research organizations, and healthcare regulators need information related to patient health status and/or delivery of healthcare (e.g., real-world data (RWD)). Such data may be used by organizations for medical treatment, diagnosis, research, regulation, and other purposes. Typically, this data needs to be manually extracted by trained experts from clinical record data that can be collected from various different sources including electronic health records (EHR), insurance billing and claims, product registries, disease registries, lab records, subject-gathered data, monitoring devices (e.g., wearable devices and biometric monitoring devices), mobile devices and/or other sources.

A system for extracting data may collect clinical record data from various sources. Values of clinical variables for subjects may then be extracted from the clinical record data and stored in an output dataset that can be provided to a healthcare organization. For example, in the context of cancer treatment, clinical variables can include a stage of cancer for a subject, a metastatic cancer diagnosis, a date of metastatic diagnosis, and/or other clinical variables. A system for extracting clinical variable values from clinical record data typically has access to large amounts of clinical record data (e.g., millions of data records) that need to be analyzed in order to extract clinical variable values. Moreover, the clinical record data may largely include unstructured data such as clinician notes, patient charts, lab records, and treatment history records.

Conventional techniques of extracting clinical variable values rely on subject matter experts who read and analyze clinical data records to manually extract values. For example, a subject matter expert (who also may be referred to as an "extractor") may read patient charts, clinician notes, lab records, insurance claims, and/or other records to determine values of various clinical variables for a subject. Given that the process of extracting clinical variable values requires manual extraction, conventional systems are only able to process a small portion of the available clinical record data (e.g., 10-20%) to extract clinical variable values. This leaves a large amount of clinical record data unprocessed and limits the amount of clinical variable values that can be extracted in a given period of time.

Moreover, manual extraction typically involves a user reviewing clinical data records through a graphical user interface (GUI) and providing input through the GUI to indicate manually extracted values. A user may be required to analyze tens or hundreds of clinical records to extract one clinical variable value. Once the user has determined a clinical variable value, the user provides input through an interface indicating the clinical variable value. Conventional system GUIs thus require a substantial amount of manual work by a user to assign a clinical variable value, and generally fail to facilitate the process of extraction for the user. Given that there are multiple clinical variables for thousands of subjects that need to be assigned values, conventional GUIs further limit the efficiency of extraction.

Machine learning technology has the capability to automate analysis of the clinical record data to extract clinical variable values and thus increase throughput of extraction. However, machine learning models are unable to predict many clinical variable values with a desired level of performance. Thus, although machine learning models can automate clinical variable value extraction, clinical variable values determined solely by prediction of machine learning models are generally not reliable enough to replace manual extraction by experts. For example, an output dataset consisting of clinical variable values for subjects predicted using one or more machine learning models may not be sufficiently reliable for use of the data in treatment and/or research.

To address the above-described shortcomings of conventional techniques, the inventors have developed techniques that significantly increase the amount of clinical record data from which clinical variable values can be extracted in a given period of time. Some embodiments increase the number of clinical variable values that can be produced in a period of time by 300% to 500% relative to conventional techniques. This in turns allows a larger percentage of available clinical record data to be processed for extraction of clinical variable values.

The techniques enable the use of machine learning models in predicting values of the clinical variables while maintaining a desired quality (e.g., accuracy) of the clinical variable values. As a result, the techniques increase the throughput of clinical record data that can be processed by a system for extraction of clinical variable values. The inventors recognized that, although all clinical variables cannot be reliably predicted by machine learning models, several clinical variable values can be predicted with a high level of confidence. Having recognized this, the inventors developed a hybrid system that intelligently utilizes machine learning model prediction to assign clinical variable values for some subjects while using manual extraction for other subjects. For certain clinical variables, the hybrid system decides between assigning a machine learning model predicted value or obtaining a manually extracted value based on a confidence in the predicted value. The hybrid system enables use of machine learning to automate extraction of certain clinical variable values for several subjects that otherwise would have had to be manually extracted by users (e.g., experts) by reviewing clinical record data.

In the hybrid system, certain clinical variables are designated as hybrid variables that are assignable by either machine learning model prediction or manual extraction. The hybrid variables are clinical variables that can be reliably predicted by a machine learning model. Accordingly, the system can assign a machine learning predicted model value or a manually extracted value to a hybrid variable for a subject. To determine a hybrid variable value for a subject, the system processes clinical record data associated with the subject using a machine learning model to obtain a predicted value and a confidence score associated with the predicted value. The hybrid system uses the confidence score to determine whether to assign a machine learning model predicted hybrid variable value for a subject. When the confidence score is sufficiently high, the system automatically assigns the predicted value to the hybrid variable for the subject. Otherwise, the hybrid system assigns a manually extracted value to the hybrid variable for the subject.

The techniques further use machine learning to configure a GUI through which a user can provide input indicating extracted clinical variable values to reduce the workload required of the user. The techniques use machine learning predicted hybrid variable values that have sufficiently high confidence to automatically populate hybrid variable values in the GUI. The techniques further configure the GUI to: (1) indicate when a hybrid variable value is machine learning model predicted; and (2) restrict user modification of predicted hybrid variable values that have a high degree of confidence. For example, the GUI may restrict user modification of a predicted hybrid variable value by preventing modification, requiring submission of a request for modification, or requesting additional input confirming modification. The GUI provides guidance to users in extraction of clinical variable values while eliminating large amounts of clinical record data analysis and input submission that would otherwise need to be performed through the GUI.

FIG. 1A illustrates manual extraction of clinical variable values from clinical record data. As illustrated in FIG. 1A, there are millions of clinical data records 100 that need to be analyzed in order to extract clinical variable values for subjects. Typically, in order to determine clinical variable values for a subject, a user (e.g., a trained expert) reviews clinical record data associated with the subject and determines the clinical variable values. For example, the user may view clinical notes, diagnosis records, prescription records, and/or other types of clinical records through one of the user devices 102. The user manually reads through the clinical record data to determine clinical variable values for the subject, and then manually assigns the determined clinical variable values in a GUI. For example, the user may type in a clinical variable value, select from multiple possible values of a clinical variable, or provide input in another manner to assign a value to a clinical variable. The assigned clinical variable values are then stored in an output dataset 104. For example, the output dataset 104 may be a set of real-world data (RWD) that can be provided to an entity (e.g., a hospital, pharmaceutical company, or other organization) for use in medical diagnosis, medical treatment, development of treatments, life science research, and/or another purpose.

As an illustrative example, a user may assign values of clinical variables associated with a subject who is undergoing diagnosis and treatment for cancer. The user may need to review clinical record data to determine values of the following clinical variables: cancer stage, whether the subject has a metastatic diagnosis, and a metastatic diagnosis date if the subject had a metastatic diagnosis. The user may need to analyze several different records before the user has determined and assigned a value to every clinical variable for the subject.

Given the large number of clinical records, the clinical variable value extraction illustrated in FIG. 1A is limited by the rate of manual extraction that can be performed by users. The users who are extracting clinical variable values from the clinical record data do so at a rate that is far less than the rate at which clinical record data is being generated and updated. As such, there is a large backlog of clinical record data that is left extracted. For example, 80% or more of the clinical record data available for extraction may remain unprocessed for extraction of clinical record variable values. The limited rate of manual extraction thus limits: (1) the number of clinical records that can be processed for extraction of clinical variable values; and (2) the amount of clinical record data associated with a particular subject that can be processed for extraction of clinical variable values.

Figure 1B:
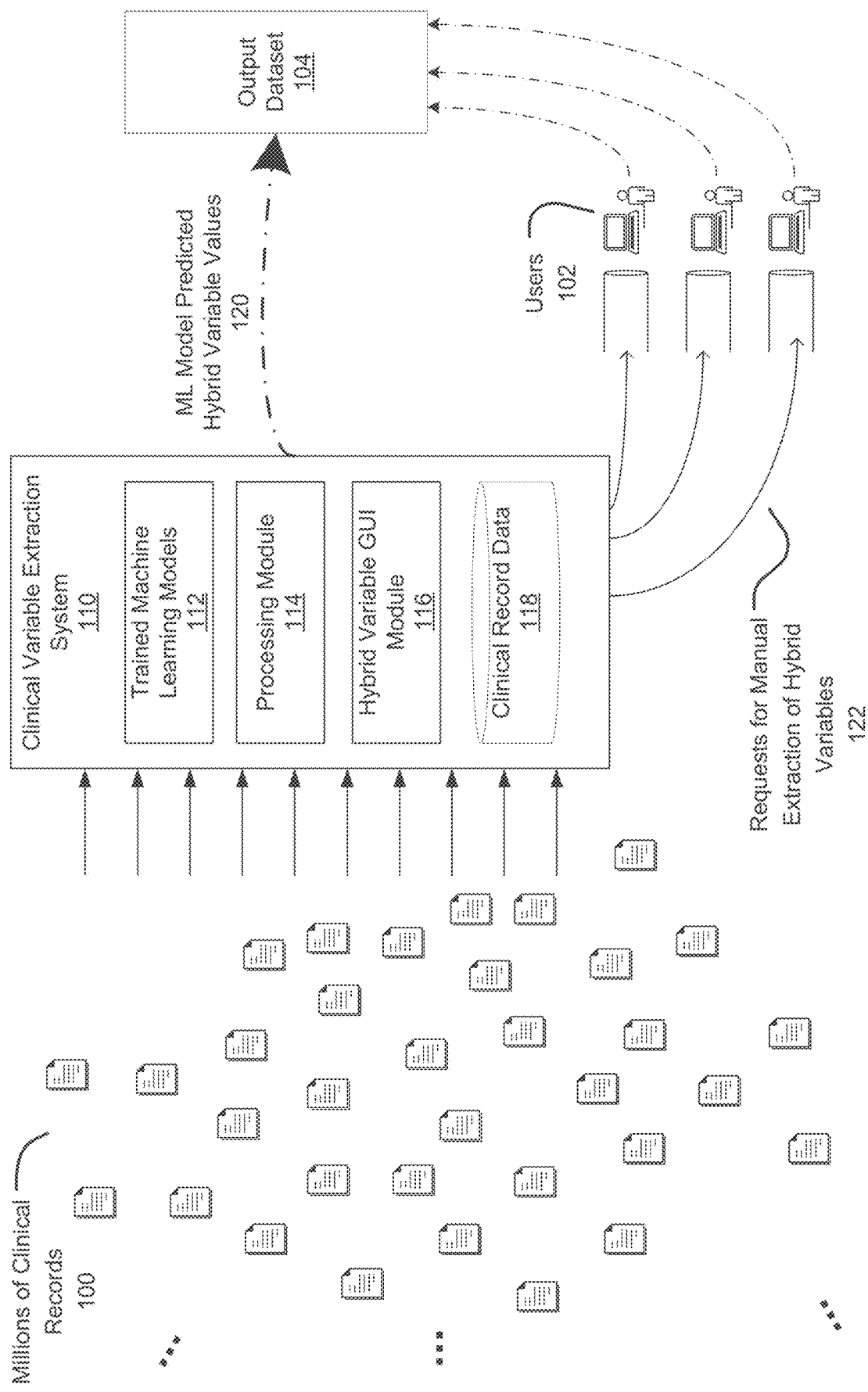
FIG. 1B is a diagram of a clinical variable extraction system of some embodiments introduced into the environment of FIG. 1A.

FIG. 1B is a diagram of a clinical variable extraction system 110 of some embodiments in the environment of FIG. 1A. The clinical variable extraction system 110 includes trained machine learning models 112, a record processing module 114, a hybrid variable GUI module 116, and a datastore 118.

In some embodiments, the clinical variable extraction system 110 may be configured to obtain clinical data records. The clinical variable extraction system 110 may be configured to communicate with one or more external systems to obtain the clinical data records. In some embodiments, the record processing module 114 may be configured to obtain the clinical data records from one or more EHR systems. For example, the clinical variable extraction system 110 may access medical notes and/or other records from an EHR system.

In some embodiments, the clinical variable extraction system 110 may be configured to transmit requests for data to an external system. For example, the clinical variable extraction system 110 may transmit queries that, when executed, return requested clinical record data. In another example, the clinical variable extraction system 110 may transmit requests through an application program interface (API). In some embodiments, the clinical variable extraction system 110 may be configured to transmit requests for clinical record data through a communication network (e.g., the Internet).

In some embodiments, the clinical variable extraction system 110 may be configured to store obtained clinical record data in data storage 118 of the clinical variable extraction system 110. In some embodiments, the clinical variable extraction system 110 may be configured to organize storage of the clinical record data by subject. The clinical variable extraction system 110 may be configured to store clinical record data mapped to identifications of subjects that the clinical record data is associated with. For example, the clinical variable extraction system 110 may map clinical record data associated with a subject to an identification (e.g., name, patient ID, or other suitable identification) of the subject.

The clinical variable extraction system 110 allows large amounts of the clinical variable value extraction process to be automated. The clinical variable extraction system 110 may be configured to use a hybrid approach that allows certain clinical variable values to be extracted automatically. Certain clinical variables may be designated as hybrid variables that can be assigned by either machine learning model prediction or by manual extraction. The clinical variable extraction system 110 can automatically assign a hybrid variable a machine learning model predicted value when the clinical variable extraction system 110 is sufficiently confident in the machine learning model prediction. This allows the clinical variable extraction system 110 to either bypass manual extraction of clinical variables for at least some subjects and/or guide a user in extraction through a GUI.

The trained machine learning models 112 may include machine learning models that are trained to predict values of various hybrid variables. The clinical variable extraction system 110 may be configured to store learned parameters of the trained machine learning models 112 obtained by application of learning techniques to training data. For example, the trained machine learning models 112 may be obtained by applying supervising, unsupervised, and/or semi-supervised learning techniques to training data to obtain the learned parameters.

In some embodiments, the trained machine learning models 112 may include a machine learning model for each of multiple hybrid variables. For example, the trained machine learning models 112 may include a machine learning model trained to extract a cancer stage from clinical record data, a machine learning model trained to extract a metastatic diagnosis from clinical record data, and a machine learning model trained to extract metastatic diagnosis date from clinical record data. The clinical variable extraction system 110 may be configured to store, for each machine learning model, an indication of a hybrid variable that the machine learning model is trained to predict. In some embodiments, a trained machine learning model may be trained to predict values of multiple hybrid variables.

In some embodiments, a clinical variable may be designated as a hybrid variable when it is determined that a machine learning model can reliably predict a value of the hybrid variable for subjects. In some embodiments, a clinical variable may be designated a hybrid variable when a machine learning model generates confidence scores associated with predictions of the clinical variable that are sufficiently informative in determining when the clinical variable should be manually extracted. For example, a given clinical variable may be designated a hybrid variable when it is predicted correctly with a threshold confidence score for a certain percentage of subjects in a test dataset. The test dataset may include clinical record data associated with the subjects and labels that can be used to determine whether a machine learning model prediction of the clinical variable for a given subject is correct. An example process of generating a test data set is described herein with reference to FIG. 6. In some embodiments, a clinical variable may be designated a hybrid variable when the machine learning model meets a minimum level of prediction performance for the hybrid variable. For example, a clinical variable may be designated a hybrid variable when the machine learning model meets a threshold accuracy, precision, and/or recall. In some embodiments, one or more other suitable metrics may be used to determine whether values of a clinical variable can be predicted by a machine learning model reliably enough to be designated a hybrid variable.

A machine learning model of the trained machine learning models 112 may be trained to predict a hybrid variable using various techniques. In some embodiments, the machine learning model may be trained using a set of training data including target hybrid variable values for multiple subjects to use as labels in performing a supervised learning technique. The target hybrid variable values may be determined by subject matter experts. For example, the machine learning model may be trained by performing stochastic gradient descent in which the parameters of the machine learning model are learned by iteratively: (1) processing input clinical record data samples using the machine learning model to obtain predicted hybrid variable values; (2) comparing the predicted hybrid variable values to values manually extracted from the clinical record data sample; and (3) updating the parameters of the machine learning model based on a difference between the predicted values and the manually extracted values.

In some embodiments, the trained machined learning models 114 may output confidence scores associated with their predicted values. A confidence score with a machine learning model predicted value of a hybrid variable may be used by the clinical variable extraction system to determine whether the predicted hybrid variable value is sufficiently reliable to assign to a subject (e.g., in output dataset 104). For example, a machine learning model may output a probability value for each of multiple classes. The class having the greatest probability value may be the predicted value of the machine learning model. The probability value associated with the predicted value may be the confidence score associated with the predicted value.

A threshold confidence score may be determined for each hybrid variable. The threshold confidence score may be used to determine whether a predicted hybrid variable value is to be assigned for a subject, or if a manually extracted hybrid variable value is to be assigned for the subject. In some embodiments, each hybrid variable has an associated confidence score threshold that is used to determine whether a machine learning model predicted value of the hybrid variable can be assigned for a subject. In some embodiments, a single confidence score threshold may be used for all hybrid variables. An example process for determining a confidence score threshold for a hybrid variable is described herein with reference to FIG. 7.

In some embodiments, the trained machine learning models 112 may include one or more machine learning models that are trained to process unstructured data to predict hybrid variable value(s). For example, the machine learning model(s) may include deep learning model(s) that analyze unstructured data that predict hybrid value(s). Example machine learning models that may be included in the clinical variable extraction system 110 are described in U.S. patent application Ser. No. 16/936,985 filed on Jul. 23, 2020, U.S. patent application Ser. No. 16/971,238 filed on Oct. 29, 2019, and U.S. patent application Ser. No. 17/345,448 filed on Jun. 11, 2021, each of each is incorporated by reference herein.

The processing module 114 may be configured to process clinical record data to extract clinical variable values (including hybrid variable values) for subjects from clinical record data. In some embodiments, the processing module 114 may be configured to automatically extract a hybrid variable value from clinical record data associated with a subject by: (1) processing, using a machine learning model trained to predict a value of the hybrid variable, the clinical record data to obtain a predicted hybrid variable value and an associated confidence score; and (2) determining, using the confidence score, whether to set the hybrid variable value for the subject to the predicted hybrid variable value. In some embodiments, the processing module 114 may be configured to determine whether to set the hybrid variable for the subject to the predicted hybrid variable value by determining whether the confidence score meets a threshold confidence score. When the processing module 114 determines that the confidence score meets the threshold confidence score, then the processing module 114 determines to set the hybrid variable value for the subject to the predicted hybrid variable value. When the processing module 114 determines that the confidence score does not meet the threshold confidence score, then the processing module 114 determines to not set the hybrid variable value for the subject to the predicted hybrid variable value.

When the processing module 114 determines to set a hybrid variable value for a subject to a predicted hybrid variable value, the processing module 114 automatically assigns the predicted hybrid variable value for the subject. For example, the processing module 114 may store the predicted hybrid variable value for the subject in the output dataset 104. As another example, the processing module 114 may configure a GUI to indicate the predicted hybrid variable value for the subject (e.g., as described herein with reference to the hybrid variable GUI module 116). The configured GUI may thus allow a user to bypass steps of extracting a value of the hybrid variable from clinical record data.

When the processing module 114 determines to not set a hybrid variable value for a subject to a predicted hybrid value, the processing module 114 obtains a manually extracted value of the hybrid variable. In some embodiments, the processing module 114 may generate requests 122 for manually extracted hybrid values (e.g., in a GUI) and receive a response to the request (e.g., through the GUI). For example, the processing module 114 may receive, through a GUI, a manually extracted hybrid variable value for a subject determined by one of the users 102. The manually extracted hybrid variable value may be written to the output dataset 104.

The processing module 114 may be configured to process clinical record data associated with a subject to obtain a predicted hybrid variable value using a machine learning model. The processing module 114 may be configured to: (1) generate, using the clinical record data, input for the machine learning model; and (2) provide the generated input to the machine learning model to obtain output indicating the predicted hybrid variable value. For example, the machine learning model may be a neural network trained to process textual data to determine a stage of cancer for a subject. In this example, the processing module 114 may generate a vector representing textual information from a medical note, and provide the vector as input to the neural network. The neural network may process the vector to output a stage of cancer for the subject. The processing module 114 may use learned parameters of the neural network (e.g., weights) to process the vector to obtain the stage of cancer for the subject. The neural network may further output a confidence score (e.g., a probability value output by a softmax layer) associated with the predicted stage of cancer.

The hybrid variable GUI module 116 may be configured to generate a GUI for presentation and setting of hybrid variable values. The hybrid variable GUI module 116 may be configured to generate a GUI for a hybrid variable for a subject using a value of the hybrid variable for the subject determined by the processing module 114.

The hybrid variable GUI module 116 may be configured to generate a GUI portion indicating a predicted hybrid variable value for a subject. In some embodiments, the hybrid variable GUI module 116 may configure the GUI portion to display the predicted hybrid variable value for the subject. For example, the hybrid variable GUI module 116 may include textual information in the GUI portion indicating the predicted hybrid variable value. In some embodiments, the hybrid variable GUI module 116 may configure the GUI portion to display an indication that a displayed hybrid variable value is a machine learning model predicted value. For example, the hybrid variable GUI module 116 may include textual information in the GUI portion indicating that the displayed value is a machine learning model predicted value. As another example, the hybrid variable GUI module 116 may: (1) detect an action in the GUI (e.g., hovering a cursor over a particular graphical element); and (2) display a message indicating that that a displayed hybrid variable value is a machine learning model predicted value in response to detecting the action in the GUI.

Figure 1C:
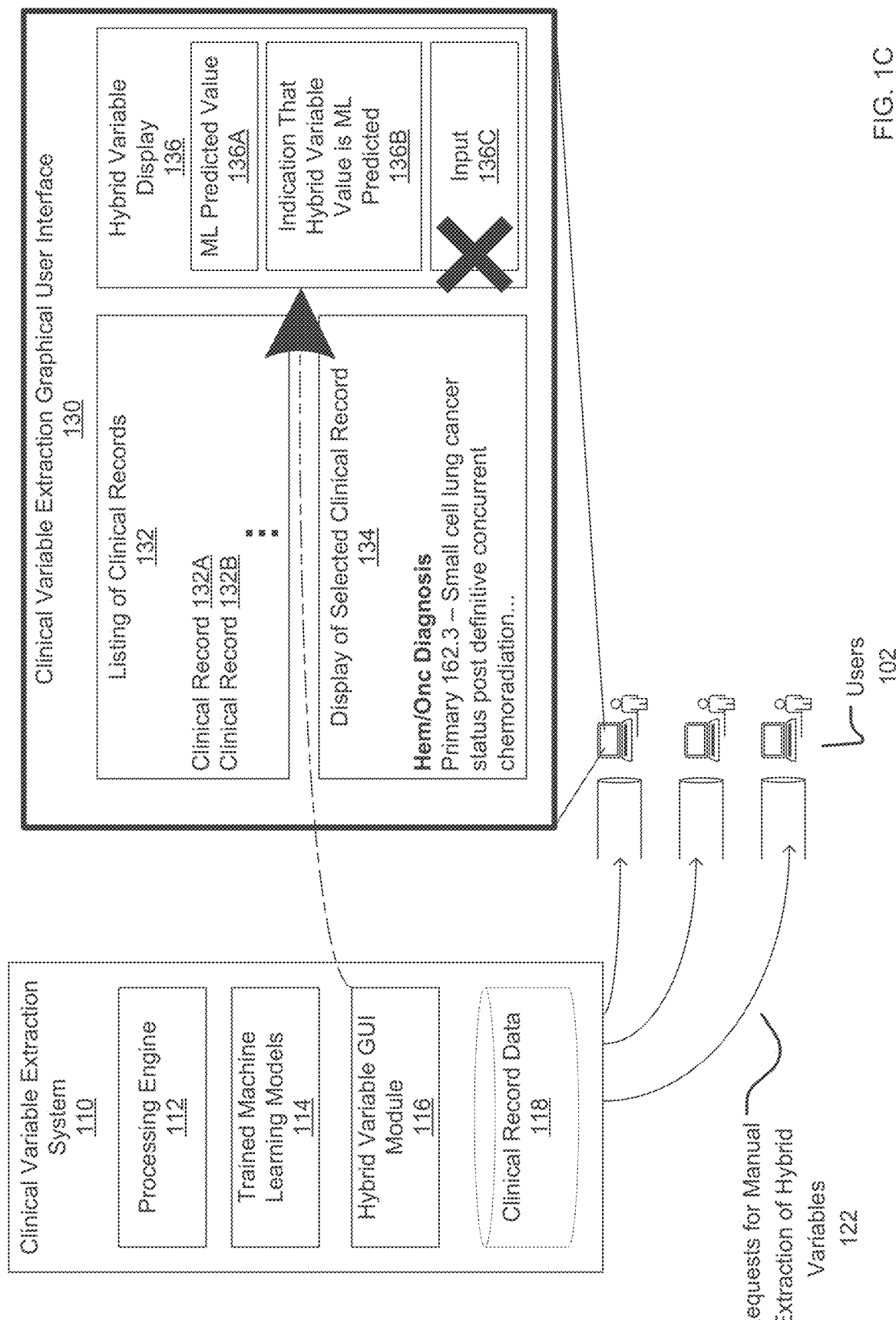
FIG. 1C depicts an example graphical user interface (GUI) generated by the clinical variable extraction system of FIG. 1B, according to some embodiments of the technology described herein.

FIG. 1C depicts an example graphical user interface (GUI) 130 generated by the clinical variable extraction system of FIG. 1B (e.g., by the hybrid variable GUI module 116), according to some embodiments. The GUI 130 includes the following GUI portions: a listing of clinical records 132, a display 134 of a selected clinical record, and a hybrid variable display 136.

The listing of clinical records 132 may allow a user (e.g., a subject matter expert) to navigate clinical record data associated with a subject. In the example of FIG. 1C, the listing 132 includes a list of clinical records. For example, the clinical record 132A may be a clinical note recorded at a first time and the clinical record 132B may be a clinical note recorded at a subsequent time. Each of the clinical records 132A, 132B may, for example, have been generated by a clinician and stored in an EHR. The listing of clinical records 132 may allow a user to select a particular record and, in response to the selection, display information from the selected record (e.g., in the display 134).

The display 134 of a selected clinical record may show information from the clinical record. For example, the display 134 may show information from a clinical note entered into an EHR system (e.g., of a medical facility). The display 134 may allow the user to read the information from one or more clinical records to extract clinical variable values for a subject. For example, the display 134 may show a clinical note selected from the listing of clinical records 132. The user may read the selected clinical note to extract clinical variable values.

The hybrid variable display 136 includes a display of a machine learning model predicted value. The hybrid variable display further includes an indication that the hybrid variable value is a machine learning model predicted value. For example, the indication 136B may be a message proximate the display of the machine learning predicted value 136A. As another example, the indication 136B may be a symbol indicative of the displayed value 136A being a predicted value. As another example, the indication 136B may be displayed in response to detecting a user action (e.g., hovering a cursor over an icon) within the GUI 130.

The hybrid variable display 136 includes a GUI portion 136C for inputting a value of the hybrid variable value. For example, the GUI portion 136C may include an interface through which a user can type in or indicate a selected hybrid variable value. As indicated by the "X", in some embodiments the hybrid variable GUI module 116 may be configured to restrict modification of a predicted hybrid variable value (e.g., when the predicted hybrid variable value is sufficiently confident). In some embodiments, the hybrid variable GUI module 116 may be configured to prevent any modification of the hybrid variable value. In some embodiments, the hybrid variable GUI module 116 may require an additional confirmation from a user when a request is received to change a hybrid variable value from a predicted value. For example, the hybrid variable GUI may display a dialogue box requesting further confirmation for a user to submit a modification to a predicted hybrid variable value. In some embodiments, the hybrid variable GUI module 116 may restrict modification to a predicted hybrid variable value by removing any option to modify the hybrid variable value.

The data storage 118 of the clinical variable extraction system 110 may comprise any suitable storage hardware. For example, the data storage 118 may comprise of one or more hard drives. In another example, the data storage 118 may comprise cloud storage that may be accessed through a communication network (e.g., the Internet). Clinical record data may be stored in the data storage 118. In some embodiments the clinical record data may be organized by subject. For example, the clinical record data 118 may be stored in tables. In another example, the clinical record data may be stored without a schema.

The output dataset 104 may include clinical variable values for multiple subjects. For example, the output dataset 104 may be a set of RWD to be provided to one or more organizations. The clinical variable extraction system 110 may be configured to provide the output dataset 104 to another entity (e.g., a system of another organization) for use by the entity. For example, the clinical variable extraction system 110 may transmit the output data set 104 to a computer system of another entity. In some embodiments, the output dataset 104 may be a table of clinical variable values for multiple different subjects. An example portion of an output data set is described herein with reference to FIG. 3.

Figure 2:
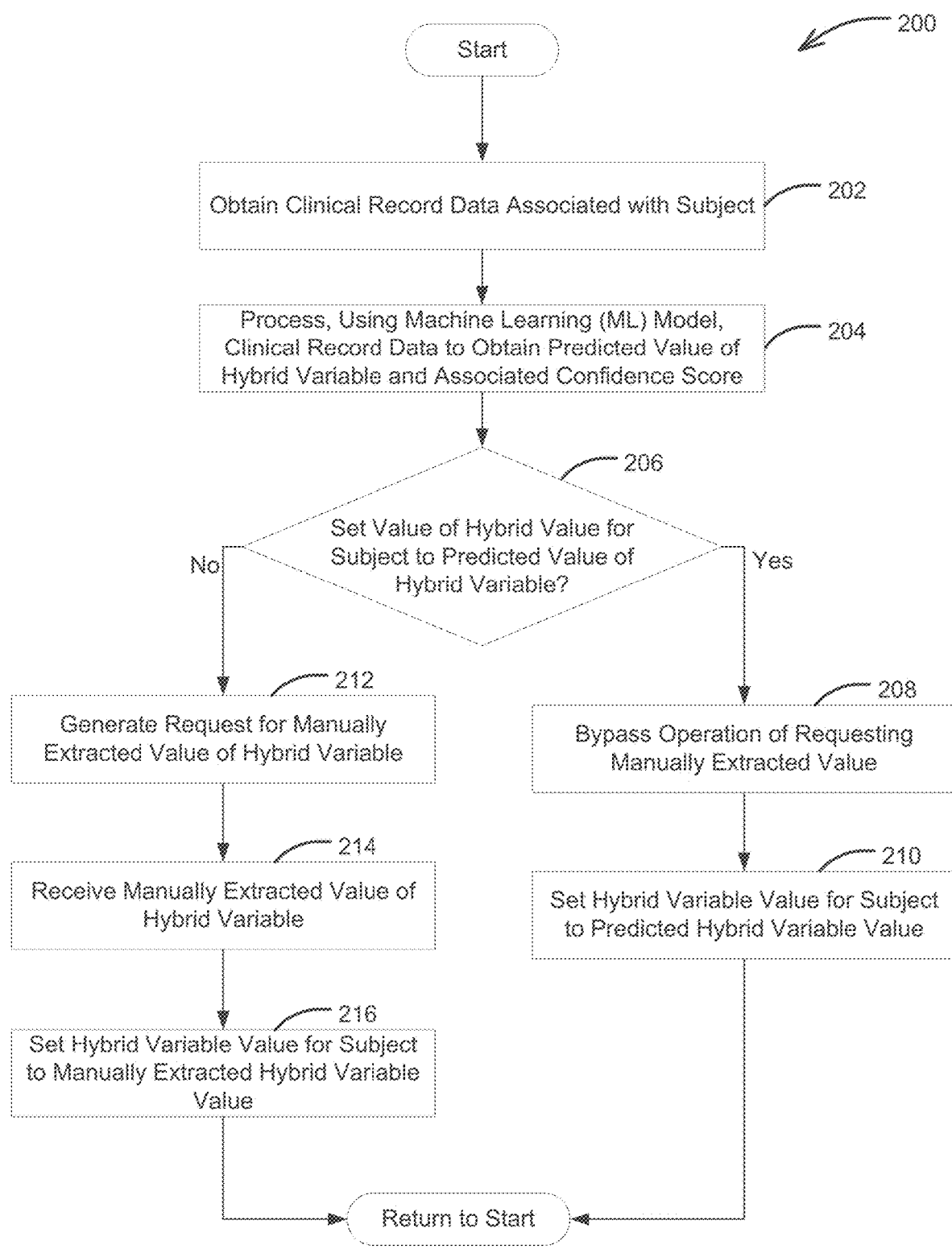
FIG. 2 is a flowchart of an example process of using machine learning to extract clinical variable values for subjects, according to some embodiments of the technology described herein.

FIG. 2 is a flowchart of an example process 200 of using a machine learning model to extract clinical variable values for subjects, according to some embodiments of the technology described herein. Process 200 may be performed by any suitable computing device. For example, the process 200 may be performed by clinical variable extraction system 110 described herein with reference to FIGS. 1A-1C.

Process 200 begins at block 202, where the system obtains clinical record data associated with a subject. In some embodiments, the system may be configured to access the clinical record data associated with the subject from a datastore (e.g., data storage 118) of the system (e.g., previously accessed from an EHR or other external system). In some embodiments, the system may be configured to obtain the clinical record data from another external system. For example, the system may transmit a request to another system and receive the clinical record data in response to the request.

Next, process 200 proceeds to block 204, the system processes, using the machine learning model, the clinical record data associated with the subject to obtain a predicted hybrid variable value for the subject and an associated confidence score. In some embodiments, the predicted hybrid variable value may be a classification by the machine learning model, and the confidence score may be a score output by the machine learning model for the classification. For example, the predicted hybrid variable value may be a cancer stage prediction and an associated probability value. As another example, the predicted hybrid variable value may be an indication of whether the subject had a metastatic cancer diagnosis.

The system may be configured to process the clinical record data by: (1) using the clinical record data to generate input for the machine learning model; and (2) providing the generated input to the machine learning model to obtain the predicted hybrid variable value. The input generated by the system may be one or more sets of feature values. For example, the system may generate a vector of feature values that can be provided as input to the machine learning model (e.g., a neural network). In some embodiments, the system may be configured to generate input representing textual information from the clinical record data. For example, the system may segment a portion of text into tokens by identifying word boundaries in text. The system may further determine a type of data record (e.g., clinical note, prescription, or other type of data) using information in the clinical record data and/or metadata associated with the clinical record data. The system may include a representation of tokens and/or a determined category in a set of feature values (e.g., a vector) that the system provides as input to the machine learning model.

The system may be configured to process an input using learned parameters of the machine learning model (e.g., by performing inference with the learned parameters). For example, the machine learning model may include a neural network with weights learned during a training process. The system may apply the weights to the generated input to determine an output of the neural network.

After obtaining the predicted hybrid variable value at block 204, process 200 proceeds to block 206 where the system determines whether to set the hybrid variable value for the subject to the predicted hybrid variable value. In some embodiments, the system may be configured to determine whether to set the hybrid variable value to the predicted hybrid variable value using a confidence score associated with the predicted hybrid variable value. The system may be configured to use the confidence score to determine whether to set the hybrid variable value to the predicted hybrid variable value by determining whether the confidence score meets a threshold confidence score determined for the hybrid variable. For example, the system may determine whether a probability value output by the machine learning model in association with the predicted value meets a threshold probability value.

When the system determines that the hybrid value for the subject is to be set to the predicted hybrid variable value, process 200 proceeds to block 208, where the system bypasses requesting of a manually extracted value. For example, the system may not generate a request for inputting of the hybrid variable value by a user in a GUI. Process 200 then proceeds to block 210 where the system sets the value of the hybrid value for the subject to the predicted hybrid variable value. In some embodiments, the system may be configured to generate a GUI or portion thereof when a hybrid variable value is set to the predicted hybrid variable value (e.g., as described herein with reference to FIG. 8. The system may be configured to set the hybrid variable value in an output dataset to the predicted hybrid variable value.

When the system determines that the hybrid value for the subject is not to be set to the predicted hybrid variable value, process 200 proceeds to block 212, where the system generates a request for a manually extracted value of the hybrid variable. For example, the system may generate an interface in a GUI that allows a user (e.g., subject matter expert) to provide a manually extracted value of the hybrid variable. Next, at block 214, the system receives the manually extracted value of the hybrid variable (e.g., provided through a GUI). The system sets the hybrid variable value for the subject to the manually extracted hybrid variable value. For example, the system may set the hybrid variable value in an output dataset to the manually extracted hybrid variable value.

The Process 200 may be performed for multiple hybrid variables. In some embodiments, the process 200 may be performed in parallel for at least some of the hybrid variables. In some embodiments, the process 300 may be performed sequentially for at least some of the hybrid variables.

FIG. 3 is a portion of an example dataset 300 of extracted clinical variable values for multiple subjects, according to some embodiments of the technology described herein. As shown in FIG. 3, the dataset 300 includes values of clinical variables for multiple different subjects. The clinical variables are a stage of cancer, a metastatic diagnosis of cancer, and a date of metastatic diagnosis where applicable. Each of the clinical variables of the dataset 300 is a hybrid variable that can be assigned by machine learning model prediction or by manual extraction.

In the example of FIG. 3, the subject "P001" has a manually extracted cancer stage value of "IIA", a machine learning predicted value of "No" for metastatic diagnosis. The subject "P002" has a machine learning predicted value of "IVB" for cancer stage, a machine learning predicted value of "Yes" for the metastatic diagnosis, and a machine learning predicted value of "2018-05-10" for the metastatic diagnosis date. The subject "P003" has a machine learning predicted value of "II" for cancer stage, a machine learning predicted value of "Yes" for metastatic diagnosis, and a manually extracted value of "2019-03-12" for the metastatic diagnosis date. The subject "P004" has a machine learning predicted value of "II" for cancer stage and a manually extracted value of "No" for metastatic diagnosis. The subject "P004" has a manually extracted value of "IVA" for cancer stage, a manually extracted value of "Yes" for the metastatic diagnosis, and a manually extracted value of "2016-01-20" for the metastatic diagnosis date.

Figure 4:
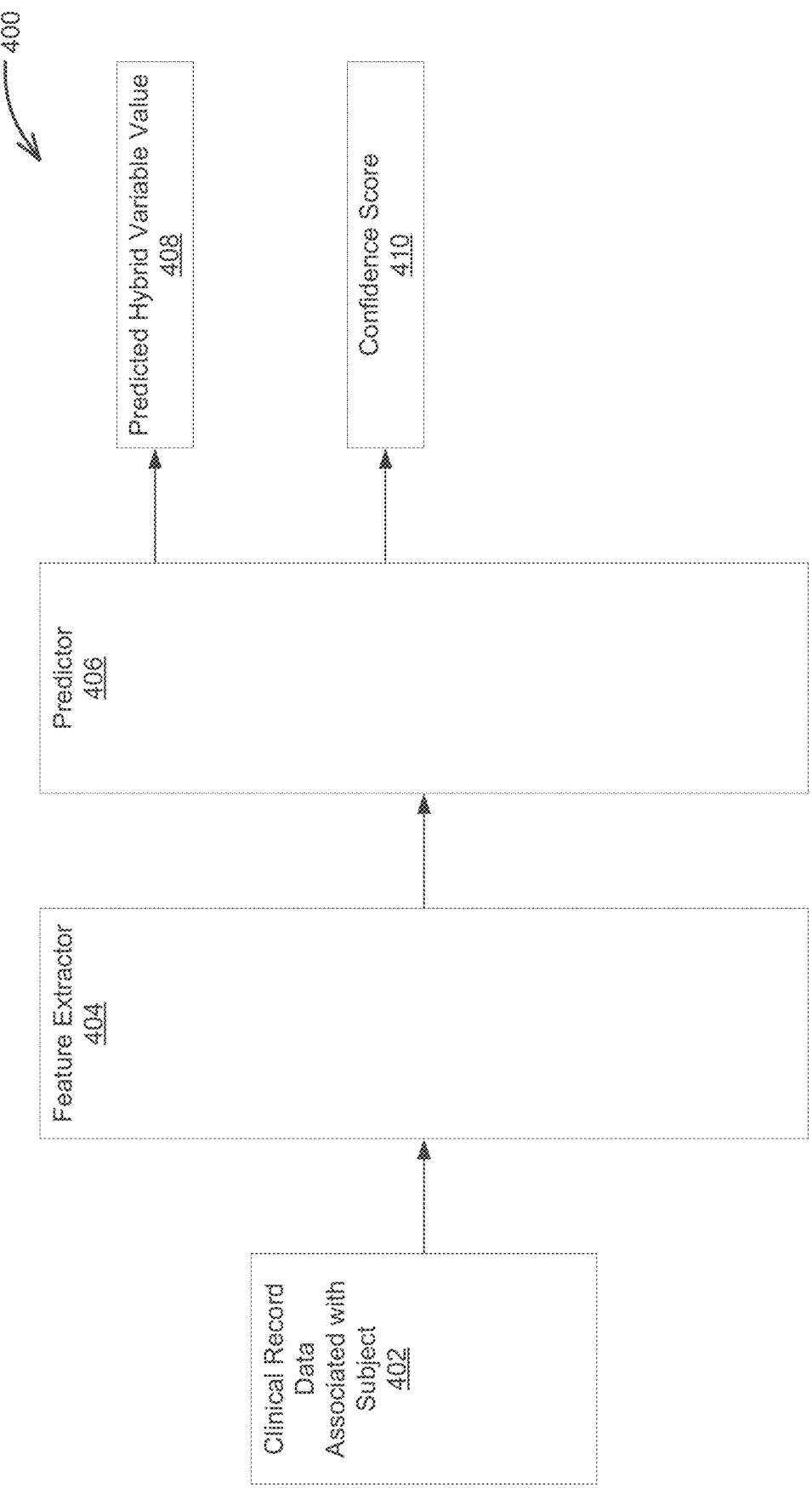
FIG. 4 is a diagram of a machine learning system for predicting a hybrid variable value, according to some embodiments of the technology described herein.

FIG. 4 is a diagram of a machine learning system 400 for predicting a hybrid variable value, according to some embodiments of the technology described herein. The machine learning system 400 may be used by the clinical variable extraction system 110, described herein with reference to FIG. 1, to determine a predicted hybrid variable value. For example, the machine learning system 400 may be used at block 206 of process 200 described herein with reference to FIG. 2. The machine learning system 400 includes a feature extractor 404 and a predictor 406.

The feature extractor 404 may be configured to generate a set of feature values using clinical record data 402 (e.g., clinical note(s)) associated with a subject. In some embodiments, the clinical record data may include textual information, and the feature extractor 404 may generate a set of feature values from the textual information. The feature extractor 404 may identify boundaries between words of the clinical record data, and organize the words into a vector (e.g., as a set of tokens). The feature extractor 404 may further convert the words into a respective representation. For example, the feature extractor 404 may map each word to a number representation, and generate a vector of the real number representations. The feature extractor 404 may provide a generated set of features to the predictor 406.

The predictor 406 may be configured to use the set of feature values to determine a predicted hybrid variable value 408 and an associated confidence score 410. In some embodiments, the predictor 406 may be a neural network that receives a vector as input. The neural network may include multiple layers with respective weights that are successively applied to inputs to the layers. The final layer of the neural network may output a prediction. For example, the final layer of the neural network may output a score (e.g., a probability value output of a softmax layer) for each of multiple classifications. The classification associated with the highest score may be the predicted hybrid variable value, and the associated score may be its confidence score.

Figure 5:
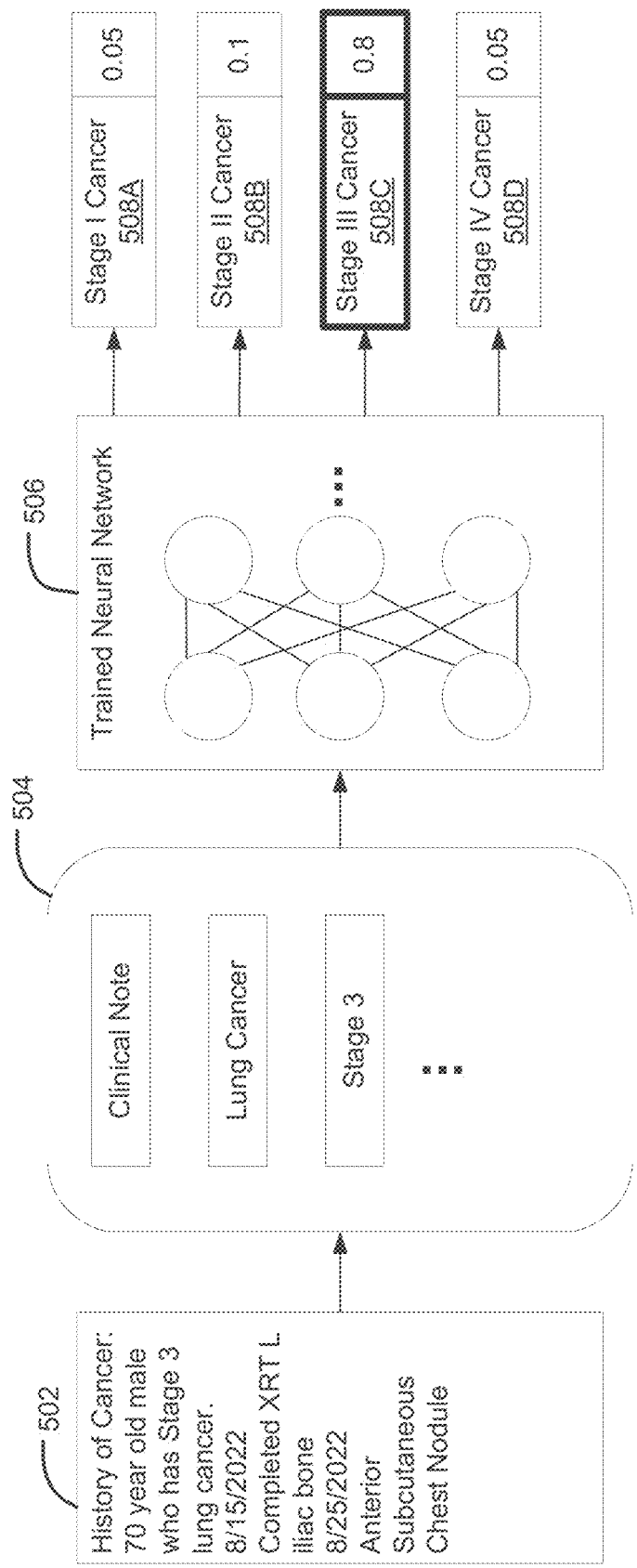
FIG. 5 illustrates example operation of the machine learning system of FIG. 4 to predict a hybrid variable value, according to some embodiments of the technology described herein.

FIG. 5 illustrates example operation of the machine learning system 400 of FIG. 4 to predict a value of the hybrid variable cancer stage from clinical record data, according to some embodiments of the technology described herein. The clinical record data 502 consists of a clinical note. The clinical note 502 is tokenized into a vector 504 of words extracted from the clinical note 502. A real number representation of the vector 504 may then be provided as input to a trained neural network 506, which outputs a probability value for each of multiple output classification. In the example of FIG. 5, the output classifications are Stage I Cancer 508A, Stage II Cancer 508B, Stage III Cancer 508C, and Stage IV Cancer 508D. In this example, the neural network 506 hybrid variable value prediction is Stage III Cancer 508C as indicated by the bolded outline in FIG. 5. The associated confidence score is 0.8, which is a probability value for the prediction outputted by the neural network 506 (e.g., from application of a softmax function to values of an output layer of the neural network 506). The confidence score 0.8 may subsequently be used to determine whether to set the cancer stage for a subject to the model predicted value, or to obtain a manually extracted value.

Figure 6:
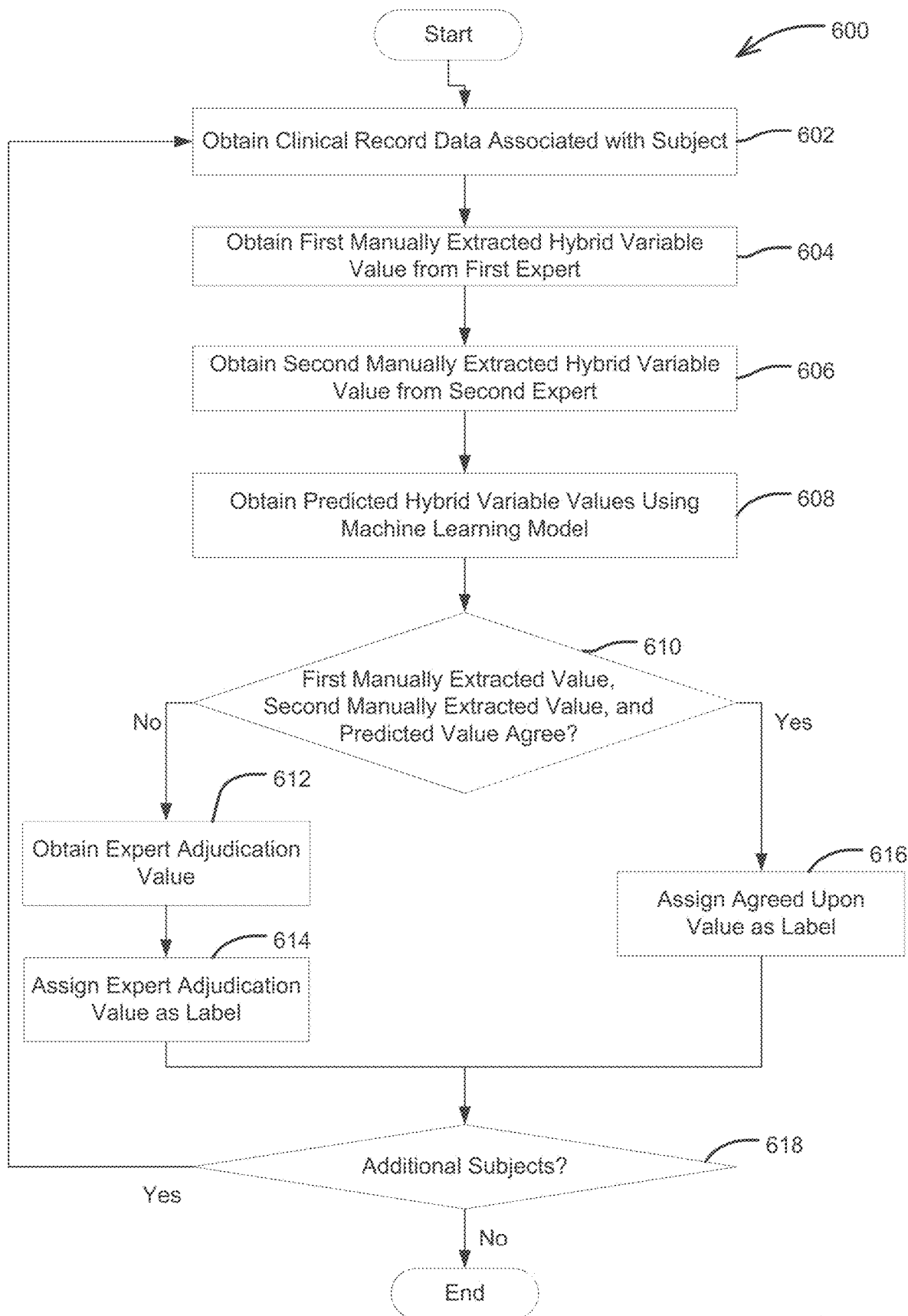
FIG. 6 is a flowchart of an example process of generating a test dataset for use in evaluating a machine learning model and/or for use in selecting a confidence score threshold, according to some embodiments of the technology described herein.

To identify a confidence score threshold to use in determining whether to set a value of a hybrid variable for a subject to a machine learning model predicted value (e.g., as described at block 206 of process 200), the accuracy of the machine learning model may be compared to that of manual extraction at different levels of confidence scores. Arbitration between manually extracted values and machine learning model predicted values requires labels (e.g., correct values) with greater accuracy than that of manual extraction and the machine learning model. The labels may be used to determine whether a machine learning model predicted value is incorrect when it is different from a manually extracted value. FIG. 6 is a flowchart of an example process 600 of generating a test dataset with labels of sufficient accuracy for evaluating a machine learning model and/or for selecting a confidence score threshold, according to some embodiments of the technology described herein. Process 600 may be performed by any suitable computing device. In some embodiments, process 600 may be performed by the clinical variable extraction system 110 described herein with reference to FIGS. 1A-1C.

Process 600 begins at block 602, where the system obtains clinical records associated with a subject. The system may access the clinical record data from the system's storage and/or from an external system. The system may access the clinical record data as described at block 202 of process 200 described herein with reference to FIG. 2.

Next, process 600 proceeds to block 604, where the system obtains a first manually extracted hybrid variable value for the subject from a first expert. In some embodiments, the system may be configured to obtain the first manually extracted hybrid value through a GUI. A user may have provided input through the GUI indicating the first manually extracted value. In some embodiments, the system may be configured to obtain the first manually extracted hybrid variable value from storage of the system. For example, the system may obtain the first manually extracted hybrid variable value from a file storing hybrid variable values that were previously manually extracted.

Next, process 600 proceeds to block 606, where the system obtains a second manually extracted variable value for the subject from a second expert. In some embodiments, the system may be configured to obtain the second manually extracted hybrid value through a GUI. A user may have provided input through the GUI indicating the second manually extracted value. In some embodiments, the system may be configured to obtain the second manually extracted hybrid variable value from storage of the system. For example, the system may obtain the second manually extracted hybrid variable value from a file storing hybrid variable values that were previously manually extracted.

Next, process 600 proceeds to block 608, where the system obtains a predicted hybrid variable value using the machine learning model. Example techniques of using a machine learning model to the predicted hybrid variable value are described herein. For example, the system may be configured to obtain a predicted hybrid variable value using the machine learning model as described at blocks 202-204 of process 200 described herein with reference to FIG. 2.

Next, process 600 proceeds to block 610, where the system determines whether the first manually extracted hybrid variable value, the second manually extracted hybrid variable value, and the predicted hybrid variable value all agree. For example, the system may determine if a classification of the machine learning model matches the first and second manually extracted values.

When the system determines that the values all agree at block 610, then process 600 proceeds to block 616, where the value is assigned as the label for the subject in the test dataset. The label may represent a true or correct value for the subject. When the system determines that the values do not agree at block 610, then process 600 proceeds to block 612, where the system obtains an expert adjudication value. The expert adjudication value may be a manually extracted value that is determined by a highly trained expert. The expert adjudication value is then assigned as the label for the subject.

After assigning a label for the subject, process 600 proceeds to block 618, where the system determines whether there are additional subjects. If there are additional subjects, then process 600 proceeds to block 602 using clinical record data for another subject. If the system determines that there is no further subjects at block 618, then process 600 ends.

Figure 7:
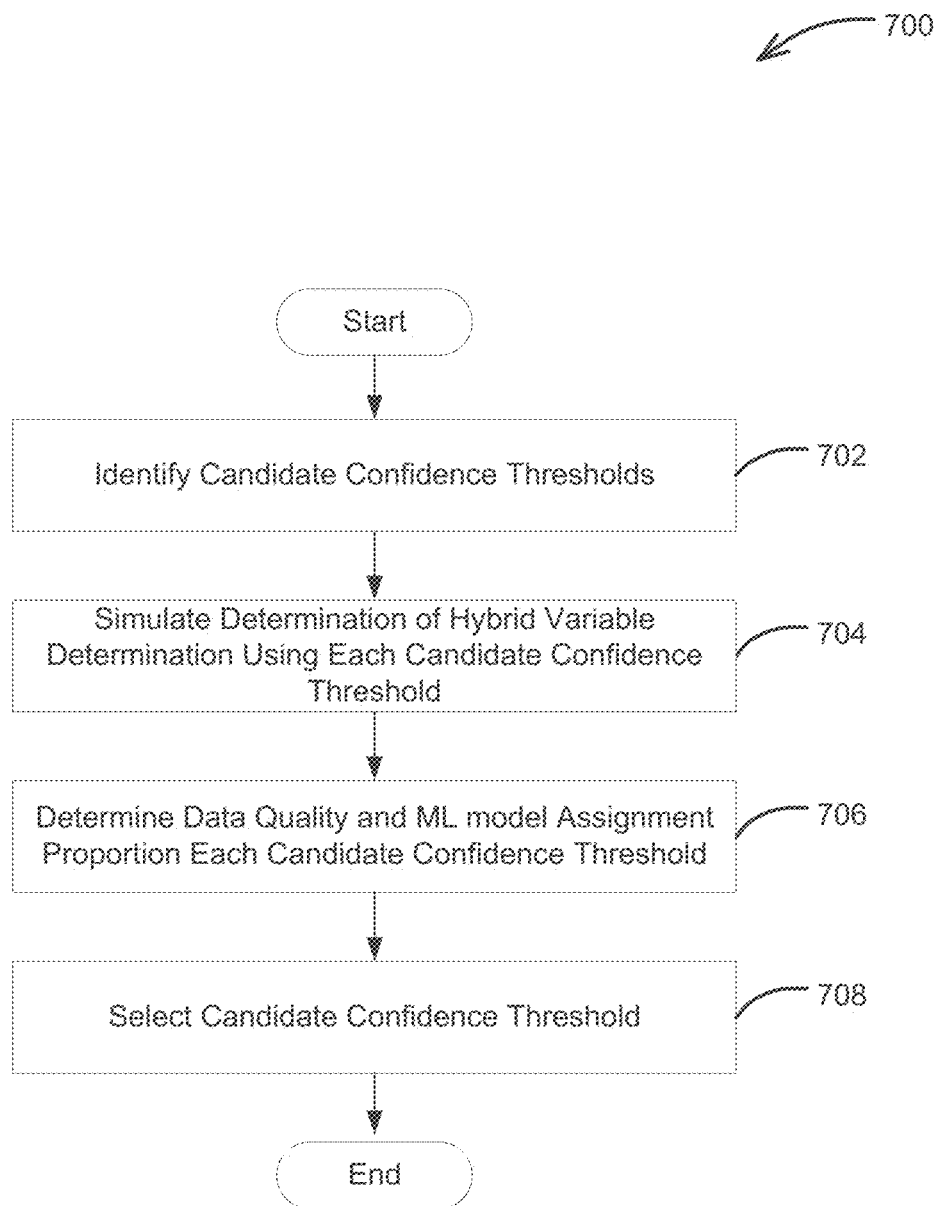
FIG. 7 is a flowchart of an example process of determining a confidence threshold for use in determining whether to use a predicted hybrid variable value, according to some embodiments of the technology described herein.

FIG. 7 is a flowchart of an example process 700 of determining a confidence score threshold for use in determining whether to set a hybrid variable value for a subject to a machine learning model predicted value, according to some embodiments of the technology described herein. Process 700 may be performed by any suitable computing device. In some embodiments, process 700 may be performed by clinical variable extraction system 110 described herein with reference to FIGS. 1A-1C.

Process 700 begins at block 700, where the system identifies candidate confidence thresholds. For example, the candidate confidence thresholds may be incrementally increasing values between 0.7 and 1.

Next, process 700 proceeds to block 704, where the system simulates extraction of hybrid variable values for a set of subjects using each of the candidate thresholds. The system may: (1) determine a hybrid variable value for each subject as performed in process 200 described herein with reference to FIG. 2; (2) and store an indication of whether the hybrid variable value set for the subject was a machine learning model predicted value or a manually extracted value. In the simulation, a previously manually extracted hybrid variable value may be used as the manually extracted value when a predicted hybrid variable value does not have a sufficiently high confidence score for assignment to a hybrid variable for a subject.

Next, process 700 proceeds to block 706, where the system determines, for each candidate confidence threshold, a data quality and a proportion of values assigned by machine learning prediction. In some embodiments, the system may be configured to determine a data quality by comparing the hybrid variable values for a candidate confidence score to a set of true hybrid variable values. The true hybrid variable values may be obtained by performing process 600 described herein with reference to FIG. 6. For example, the data quality may be a percentage of the simulated hybrid variable values that match the true values. The proportion of hybrid variables with values assigned by machine learning prediction may indicate a manual extraction workload that would be needed for prediction of values of the hybrid variable.

Next, process 700 proceeds to block 700, where the system selects a candidate confidence threshold based on the data quality and the proportion of machine learning model predicted hybrid values determined for each candidate confidence threshold. In some embodiments, the system may be configured to select the candidate confidence threshold to balance data quality and manual extraction workload.

Figure 8:
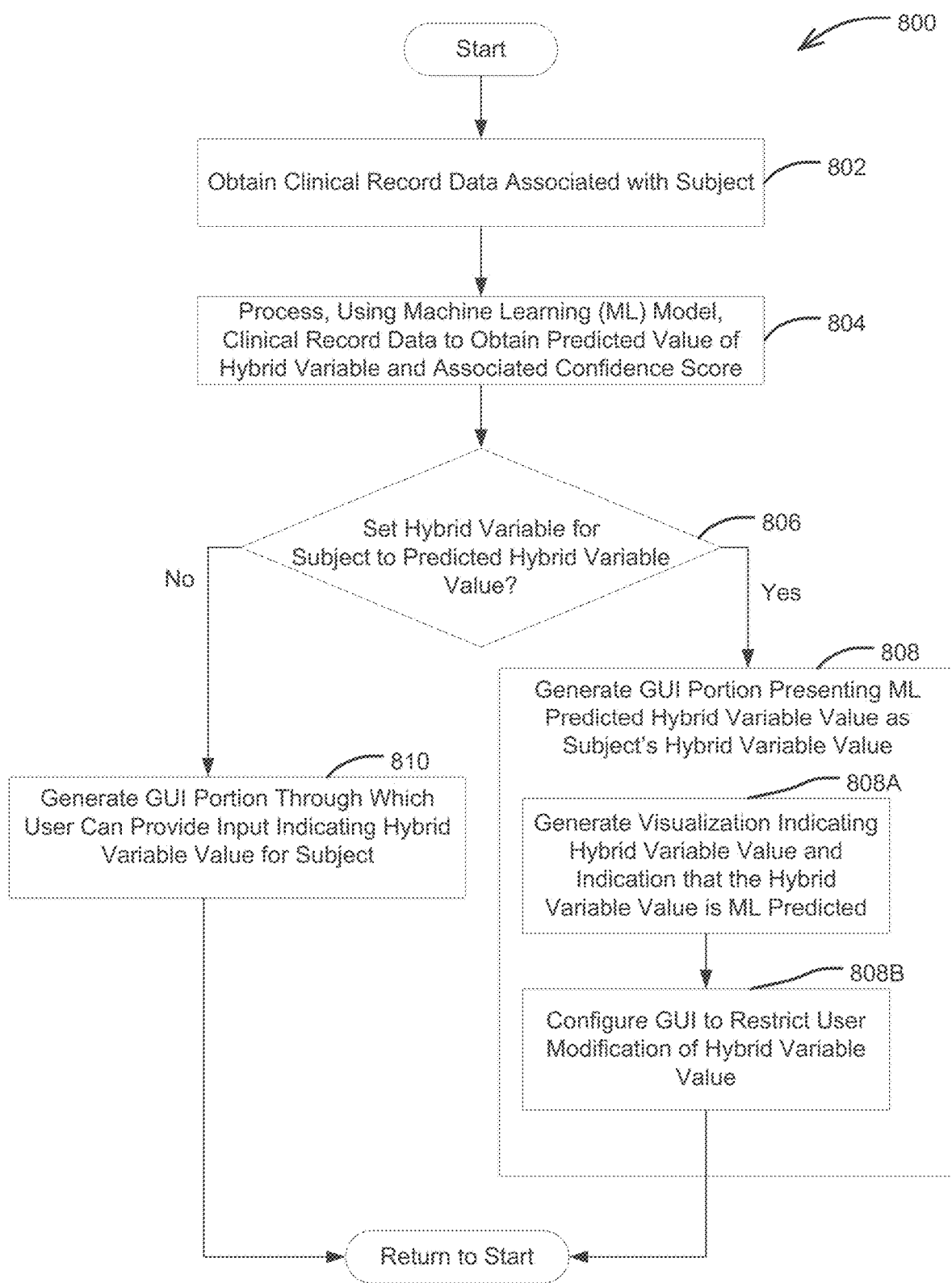
FIG. 8 is a flowchart of an example process for generating a GUI portion for displaying a hybrid variable value, according to some embodiments of the technology described herein.

FIG. 8 is a flowchart of an example process 800 for generating a GUI portion for displaying a hybrid variable value for a subject, according to some embodiments of the technology described herein. Process 800 may be performed by any suitable computing device. In some embodiments, process 800 may be performed by clinical variable extraction system 110 described herein with reference to FIGS. 1A-1C.

Process 800 begins at block 802, where the system obtains clinical record data for a subject. The system may obtain the clinical record data for the subject as described at block 202 of process 200 described herein with reference to FIG. 2.

Next, process 800 proceeds to block 804, where the system processes, using a machine learning model, the clinical record data associated with the subject to obtain a predicted hybrid variable value and an associated confidence score. The system may perform the processing as described at block 204 of process 200 described herein with reference to FIG. 2.

Next, process 800 proceeds to block 806, where the system determines whether to set the hybrid variable value for the subject to the predicted hybrid variable value. The system may determine whether to set the hybrid variable value for the subject to the predicted hybrid variable value as described at block 206 of process 200 described herein with reference to FIG. 2. For example, the system may determine whether to set the hybrid variable value for the subject to the predicted hybrid variable value based on whether the confidence score meets a threshold confidence score.

When the system determines to set the hybrid variable value for the subject to the predicted hybrid variable value, then process 800 proceeds to block 808, where the system generates a GUI portion presenting the machine learning predicted hybrid variable as the hybrid variable value for the subject.

At block 808A, the system generates a visualization indicating the hybrid variable value and an indication that the hybrid variable value is machine learning model predicted. In some embodiments, the system may be configured to display text indicating the hybrid variable value. In some embodiments, the system may be configured to display a message indicating that the value is predicted by a machine learning model. In some embodiments, the system may be configured to: (1) detect an action in the GUI (e.g., hovering over an icon in the GUI portion); and (2) display a message indicating that the value is predicted by a machine learning model in response to detecting the action.

At block 808B, the system configures the GUI to restrict user modification of the hybrid variable value. In some embodiments, the system may be configured to remove an interface through which a user can modify the hybrid variable value. For example, the system may not present a selection interface or an interface in which a value can be input. In some embodiments, the system may be configured to prevent use of a modification interface. For example, a user may be able to view an interface displaying the hybrid variable value without being about to provide input in the interface (e.g., due to the interface being grayed out). In some embodiments, the system may be configured to restrict user modification by requiring additional confirmation to modify the predicted hybrid variable value. For example, the system may: (1) detect user input requesting to change the hybrid variable value; and (2) display a dialogue box in the GUI requesting confirmation to perform the modification. As another example, the system may allow a user to submit a request to modify the predicted hybrid variable value. The system may provide a GUI through which the user can provide input requesting to modify the predicted hybrid variable value. The GUI may allow the user to provide a modified value and/or a reason for modification of the value.

In some embodiments, the system may be configured to use the confidence score associated with the machine learning model predicted hybrid variable value to determine a level of restriction to user modification of the hybrid variable value. The system may be configured to determine whether the confidence score meets a threshold confidence score. The system may be configured to prevent modification of the predicted hybrid variable value when the confidence score meets the threshold confidence score. The system may be configured to allow modification of the predicted hybrid variable value when the confidence score does not meet the threshold confidence score. For example, the system may allow modification after requesting input through a GUI requesting confirmation to perform the modification. In some embodiments, the threshold confidence score used in determining whether to allow modification of a hybrid variable value by a user may be different than one used at block 806 to determine whether to set the value of the hybrid variable for the subject to the predicted hybrid variable value.

In some embodiments, the system may be configured to allow certain users to modify a predicted hybrid variable value irrespective of the confidence score. For example, the system may designate certain users as experts and grant such experts permission to override the predicted hybrid variable value. A user designated as an expert may override the predicted hybrid variable value even when the confidence score associated with the predicted value meets a threshold score (e.g., as determined at block 806).

When the system determines not to set the hybrid value for the subject to the predicted hybrid variable value at block 806, then process 800 proceeds to block 810, where the system generates a GUI portion through which a user can provide input indicating the hybrid variable value for the subject. The GUI portion may include a portion through which the user can indicate a manually extracted value (e.g., determined by analyzing clinical record data). For example, the system may provide an interface where the user can select from multiple options. As another example, the system may provide an interface through which the user can type in a value of a hybrid variable.

Figure 9:
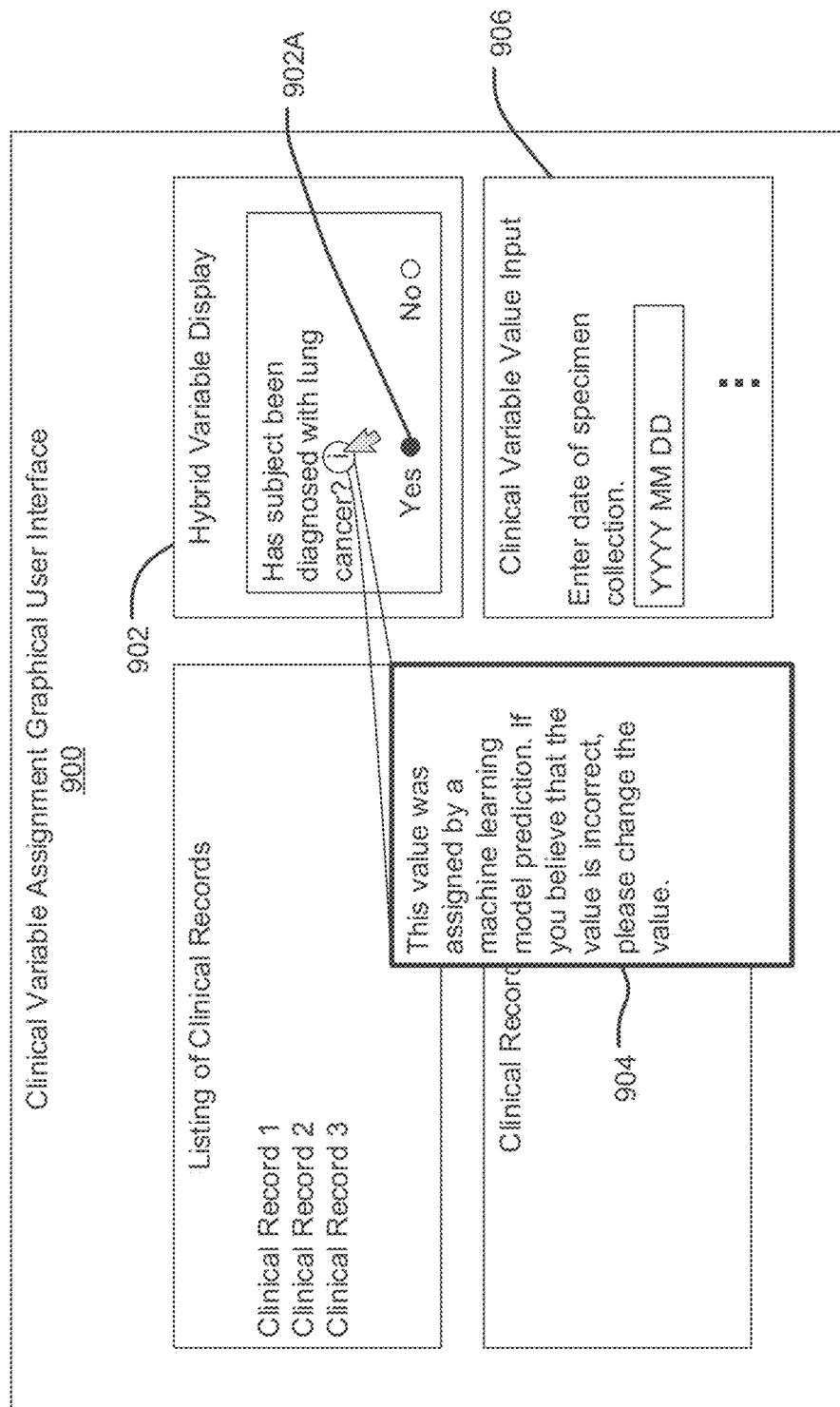
FIG. 9 is an example GUI including a portion displaying a predicted hybrid variable value for a subject and indicating that the predicted hybrid variable value was assigned by machine learning model prediction, according to some embodiments of the technology described herein.

FIG. 9 is an example GUI 900 including a portion 902 displaying a predicted hybrid variable value, according to some embodiments of the technology described herein. In some embodiments, the GUI 900 may be generated by the clinical variable extraction system 110 described herein with reference to FIGS. 1A-1C. In the example of FIG. 9, the hybrid variable is whether the subject was tested for a BRAF mutation. As shown in FIG. 9, the GUI portion 902 includes an indication 902A of the predicted value of whether the subject was tested for a BRAF mutation. The GUI portion 902 further displays a message 904 when it is detected that the cursor is over an icon in the GUI portion. The message 904 indicates that the displayed hybrid variable value is machine learning model predicted. The message 904 further indicates that the user may change the value if the user believes the value to be incorrect. In some embodiments, the message 904 may not indicate that the user may change the value (e.g., in cases where the user is not allowed to change the predicted value). As shown in FIG. 9, the GUI 900 may include an interface 906 through which a user may input values of one or more other clinical variables. The other clinical variable(s) may include non-hybrid variable(s) and/or hybrid variable(s) that have not been assigned a machine learning model predicted value.

Figure 10:
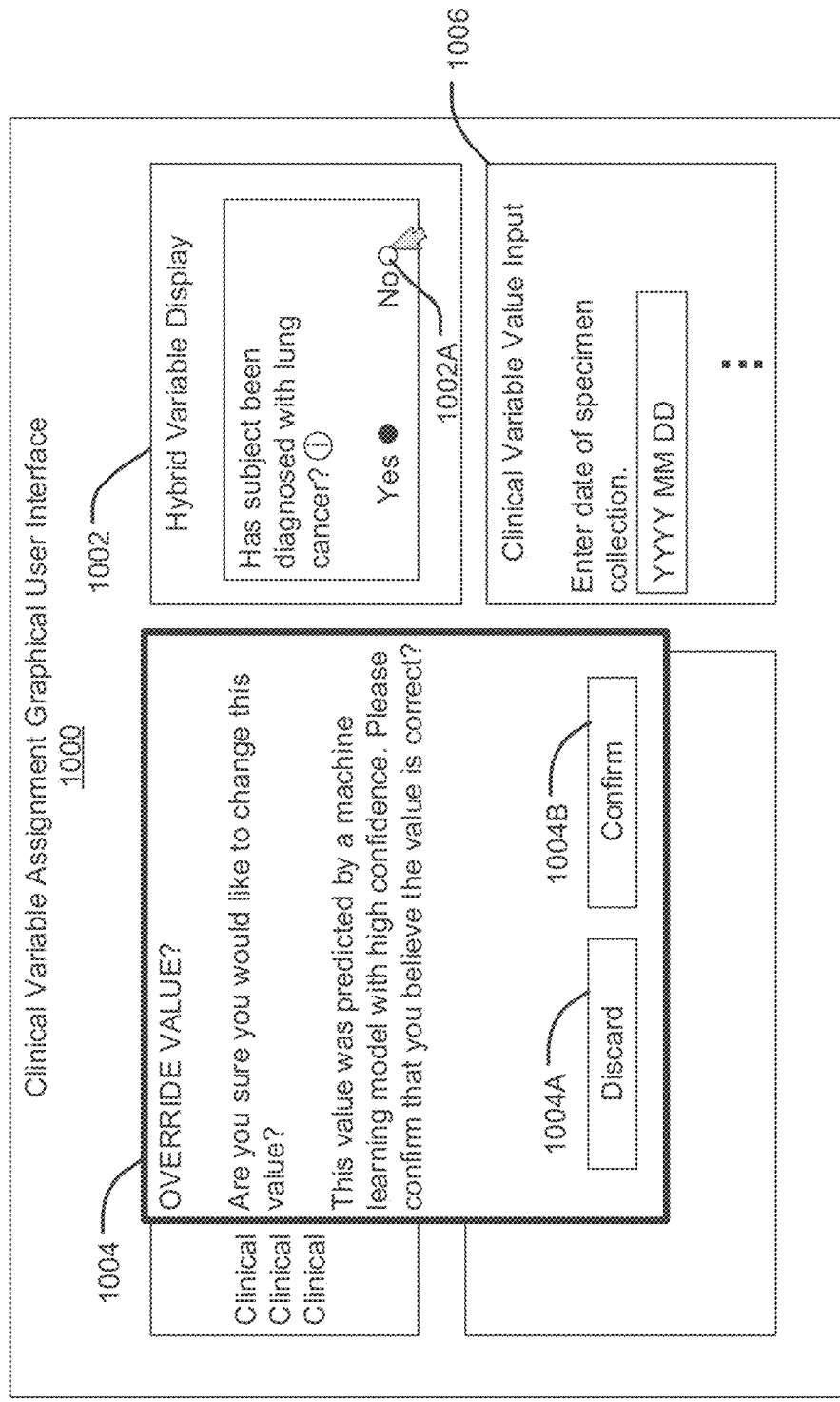
FIG. 10 is an example GUI including a portion requesting confirmation of a modification to a predicted hybrid variable value, according to some embodiments of the technology described herein.

FIG. 10 is an example GUI 1000 including a portion 1002 displaying a predicted hybrid variable value for a subject, according to some embodiments of the technology described herein. In some embodiments, the GUI 1000 may be generated by the clinical variable extraction system 110 described herein with reference to FIGS. 1A-1C. In the example of FIG. 10, the hybrid variable is whether the subject was diagnosed with lung cancer. The GUI portion 1002 allows the user to modify the hybrid variable value. As shown in FIG. 10, the user can select the graphical element 1002A (e.g., a radio button) to modify the hybrid variable of whether patient was diagnosed with lung cancer from "Yes" to "No". In response to receiving selection of the element 1002A to modify the value from "Yes" to "No", the system generates the dialogue box 1004 requesting a confirmation of the modification. The dialogue box 1004 provides an option 1004A to discard the change and an option to confirm the change 1004B. In some embodiments, the system may be configured to generate a dialogue box that allows submission of a request to change the hybrid variable value. For example, the system may provide a GUI through which a user can specify a value to modify the hybrid variable to, and a reason for requesting the modification. The system may be configured to present the submission to an expert user in a GUI through which the expert user can approve or deny the requested modification. As shown in FIG. 10, the GUI 1000 may include an interface 1006 through which a user may input values of one or more other clinical variables. The other clinical variable(s) may include non-hybrid variable(s) and/or hybrid variable(s) that have not been assigned a machine learning model predicted value.

Figure 11:
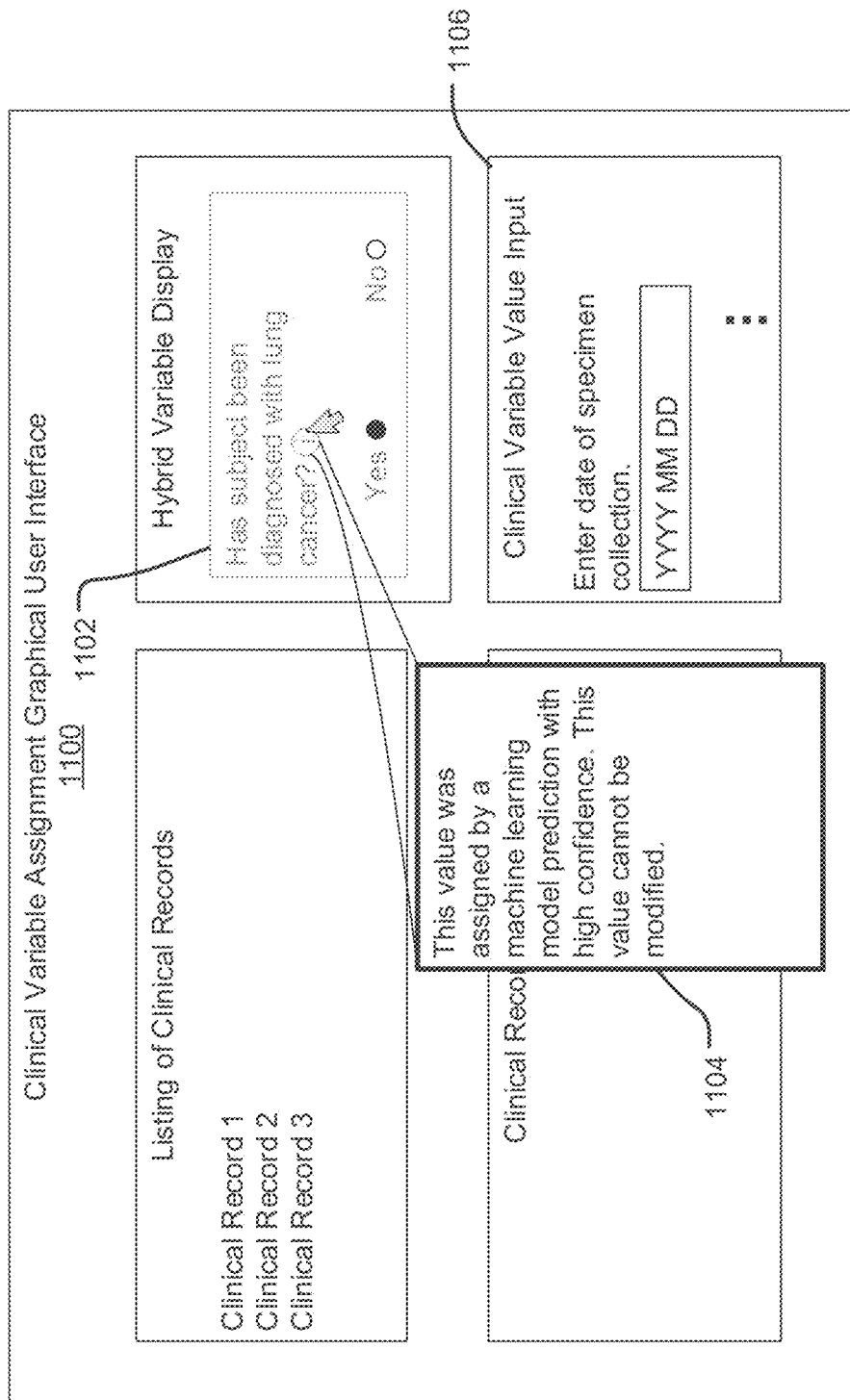
FIG. 11 is an example GUI including a portion displaying a predicted hybrid variable value for a subject in which the predicted hybrid variable value cannot be modified, according to some embodiments of the technology described herein.

FIG. 11 is an example GUI 1100 a GUI portion 1102 displaying a predicted hybrid variable value for a subject, according to some embodiments of the technology described herein. In some embodiments, the GUI 1100 may be generated by the clinical variable extraction system 110 described herein with reference to FIGS. 1A-1C. In the example of FIG. 11, the hybrid variable is whether the subject was diagnosed with lung cancer. The GUI portion 1102 prevents modification of the hybrid variable value. In this example, the modification interface is greyed out indicating that the hybrid variable value cannot be modified. The GUI portion 1102 displays a message indicating that the displayed hybrid variable value is machine learning model predicted when a cursor is over an icon in the GUI portion 1102. In some embodiments, the system may give certain users (e.g., experts) permission to modify the displayed hybrid variable value. For example, the system may provide an expert user with a different GUI from GUI 1100 through which the user can modify the hybrid variable value (e.g., GUI 900 described herein with reference to FIG. 9 or GUI 1000 described herein with reference to FIG. 10). As shown in FIG. 11, the GUI 1100 may include an interface 1106 through which a user may input values of one or more other clinical variables. The other clinical variable(s) may include non-hybrid variable(s) and/or hybrid variable(s) that have not been assigned a machine learning model predicted value.

Figure 12:
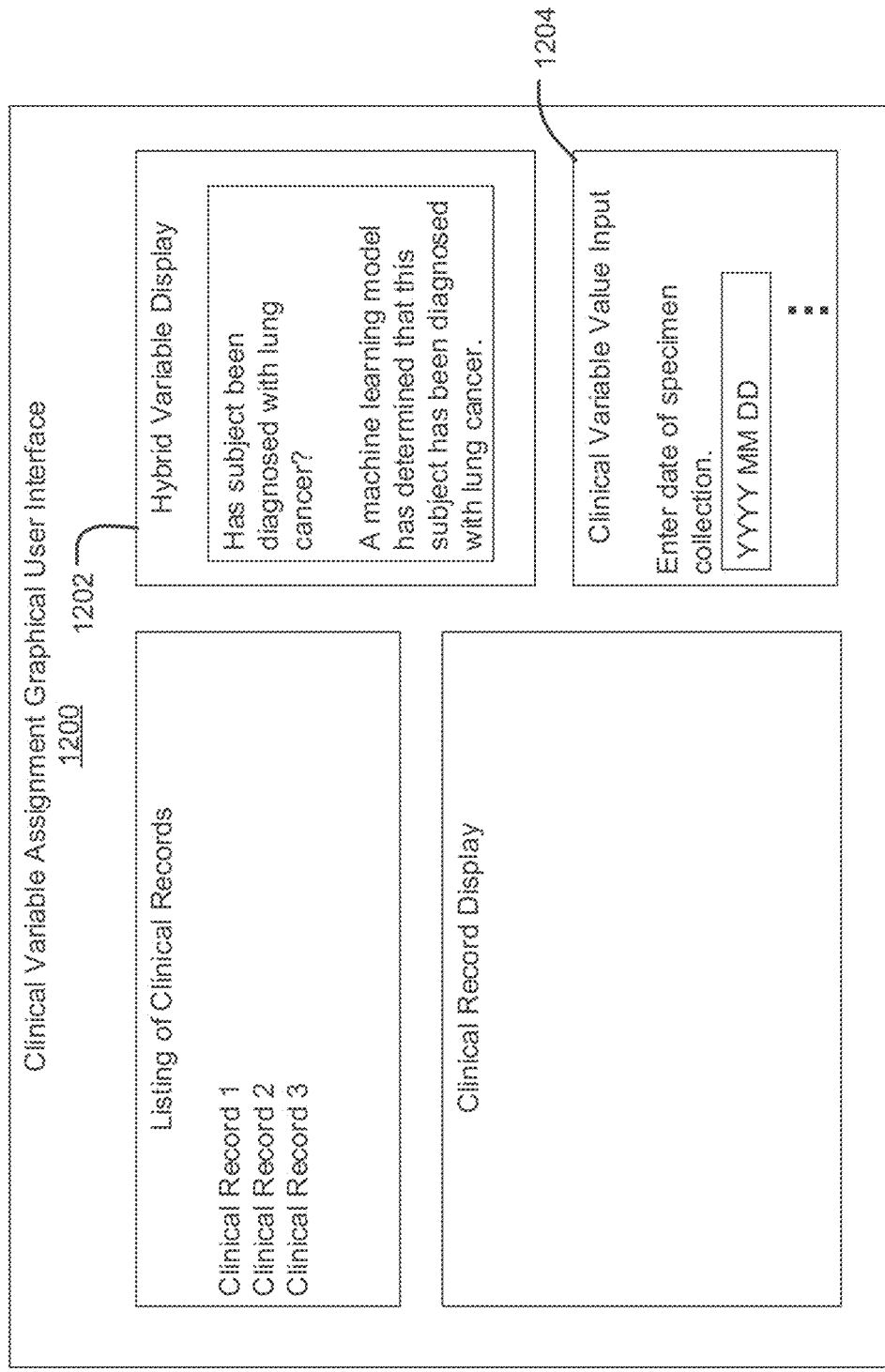
FIG. 12 is an example GUI including a portion displaying a predicted hybrid variable value for a subject in which the predicted hybrid variable value cannot be modified, according to some embodiments of the technology described herein.

FIG. 12 is an example GUI 1200 including a portion 1202 displaying a predicted hybrid variable value for a subject, according to some embodiments of the technology described herein. In some embodiments, the GUI 1200 may be generated by the clinical variable extraction system 110 described herein with reference to FIGS. 1A-1C. In the example of FIG. 12, the hybrid variable is whether the subject was diagnosed with lung cancer. The GUI portion 1202 does not include any interface for modification of the hybrid variable value. The GUI portion 1202 includes text indicating the hybrid variable value and the fact that it is machine learning model predicted. In some embodiments, the system may give certain users (e.g., experts) permission to modify the displayed hybrid variable value. For example, the system may provide an expert user with a different GUI from GUI 1200 through which the user can modify the hybrid variable value (e.g., GUI 900 described herein with reference to FIG. 9 or GUI 1000 described herein with reference to FIG. 10). As shown in FIG. 12, the GUI 1200 may include an interface 1204 through which a user may input values of one or more other clinical variables. The other clinical variable(s) may include non-hybrid variable(s) and/or hybrid variable(s) that have not been assigned a machine learning model predicted value.

Figure 13:
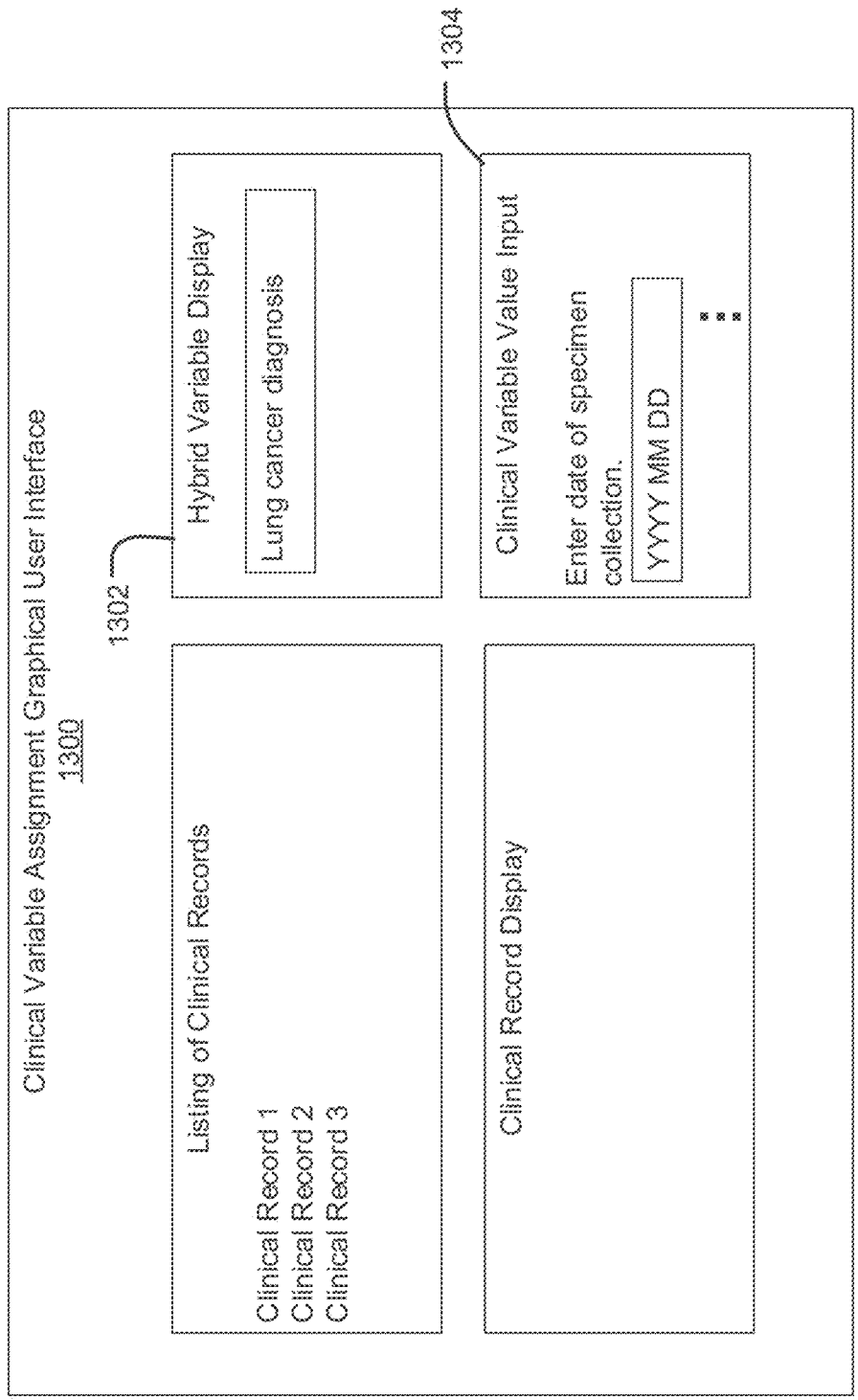
FIG. 13 is an example GUI including a portion that does not display any predicted hybrid variable value for a subject, according to some embodiments.

FIG. 13 is an example GUI 1300 including a portion 1302 that does not display any predicted hybrid variable value information for a subject, according to some embodiments. In some embodiments, the GUI 1300 may be generated by the clinical variable extraction system 110 described herein with reference to FIGS. 1A-1C. In the example of FIG. 13, the GUI does not provide any information on the predicted hybrid variable value. This allows removal of the extraction task for the hybrid variable for the user. Thus the user may not be informed of the hybrid variable value and/or its extraction by a machine learning model. In some embodiments, the system may provide certain users (e.g., experts) a different GUI than GUI 1300. For example, an expert user's GUI may display the predicted hybrid variable value and allow the expert user to modify the predicted hybrid variable value. As shown in FIG. 13, the GUI 1300 may include an interface 1304 through which a user may input values of one or more other clinical variables. The other clinical variable(s) may include non-hybrid variable(s) and/or hybrid variable(s) that have not been assigned a machine learning model predicted value.

In some embodiments, the system may be configured to set a level of restriction for a user based on a confidence score associated with a predicted hybrid variable value. The system may be configured to set the level restriction based on the confidence score by presenting a particular type of GUI to a user based on the confidence score. The system may be configured to: (1) prevent modification by the user when the confidence score is sufficiently high; and (2) allow modification or submission of a request for modification by the user when the confidence score is not sufficiently high. For example, the system may: (1) present GUI 1100, 1200, or 1300 when the confidence score meets a confidence score threshold thereby preventing modification of the hybrid variable value; and (2) present GUI 900 or 1000 when the confidence score does not meet the confidence score threshold. In some embodiments, the threshold confidence score used for determining a type of GUI to present to a user may be different than a confidence score threshold used for determining whether a machine learning model predicted value of a hybrid variable may be assigned to the hybrid variable for a subject.

Figure 14:
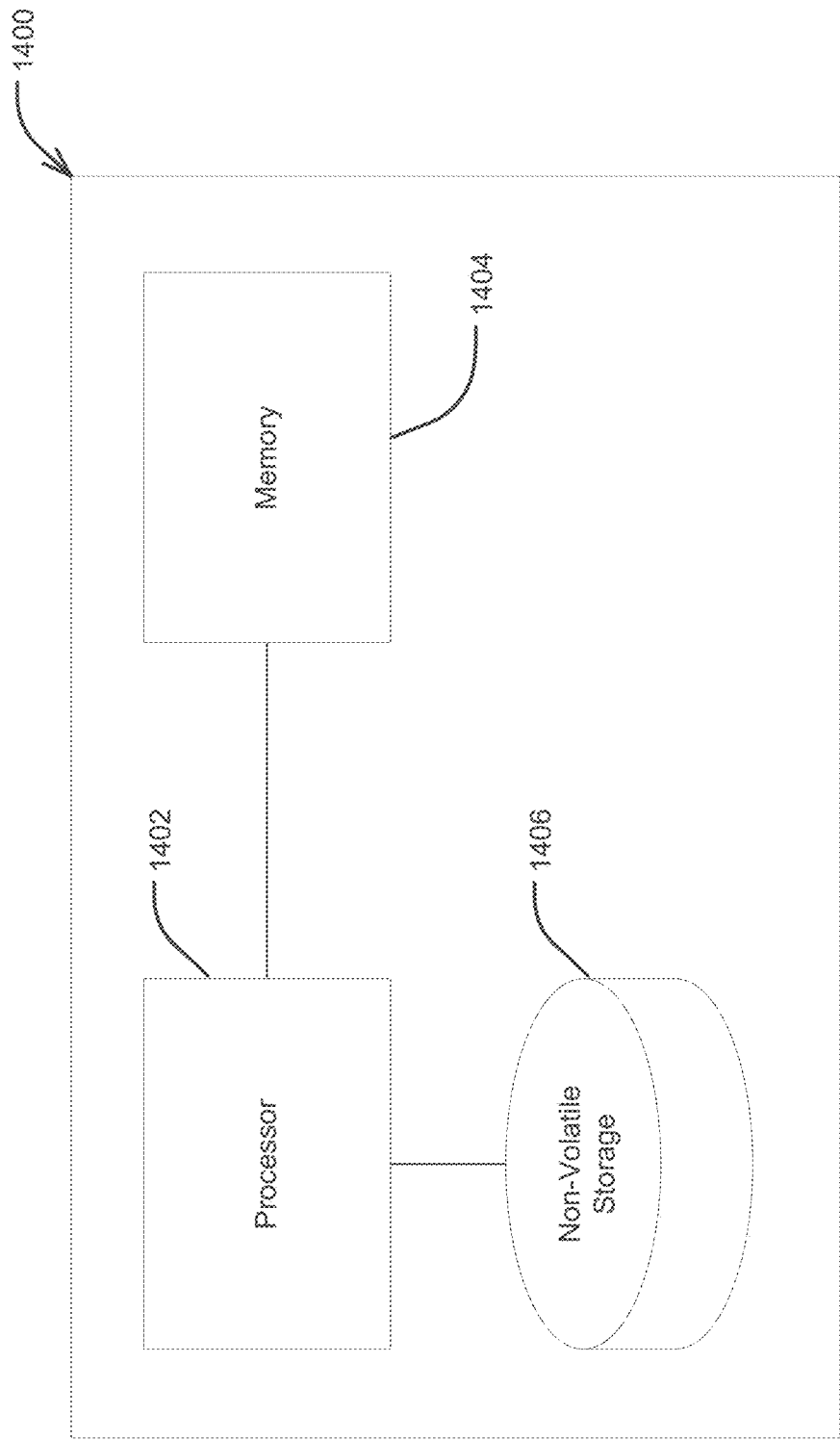
FIG. 14 is a diagram of an illustrative computing system that may be used in implementing some embodiments of the technology described herein.

FIG. 14 shows a block diagram of an example computer system 1400 that may be used to implement some embodiments of the technology described herein. The computing device 1400 may include one or more computer hardware processors 1402 and non-transitory computer-readable storage media (e.g., memory 1404 and one or more non-volatile storage devices 1406). The processor(s) 1402 may control writing data to and reading data from (1) the memory 1404; and (2) the non-volatile storage device(s) 1406. To perform any of the functionality described herein, the processor(s) 1402 may execute one or more processor-executable instructions stored in one or more non-transitory computer-readable storage media (e.g., the memory 1404), which may serve as non-transitory computer-readable storage media storing processor-executable instructions for execution by the processor(s) 1402.

Having thus described several aspects of at least one embodiment of the technology described herein, it is to be appreciated that various alterations, modifications, and improvements will readily occur to those skilled in the art.

Such alterations, modifications, and improvements are intended to be part of this disclosure, and are intended to be within the spirit and scope of disclosure. Further, though advantages of the technology described herein are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. However, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, aspects of the technology described herein may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments described above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the technology as described above. As used herein, the term "computer-readable storage medium" encompasses only a non-transitory computer-readable medium that can be considered to be a manufacture (i.e., article of manufacture) or a machine. Alternatively or additionally, aspects of the technology described herein may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the technology as described above. Additionally, it should be appreciated that according to one aspect of this embodiment, one or more computer programs that when executed perform methods of the technology described herein need not reside on a single computer or processor, but may be distributed in a modular fashion amongst a number of different computers or processors to implement various aspects of the technology described herein.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as a method, of which examples are provided herein including with reference to FIGS. 3 and 7. The acts performed as part of any of the methods may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by an "actor" or a "user". It should be appreciated that an "actor" or a "user" need not be a single individual, and that in some embodiments, actions attributable to an "actor" or a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A method of using machine learning to automatically extract values of clinical variables for a plurality of subjects from clinical record data, the method comprising:
using at least one processor to perform:
obtaining clinical record data associated with the plurality of subjects;
generating, using the clinical record, a dataset for storing values of a plurality of clinical variables, the plurality of clinical variables comprising:
a subset of clinical variables designated as hybrid variables that can have their values assigned by machine learning model prediction or by manual extraction; and
a subset of clinical variables designated as non-hybrid variables that cannot have their values assigned by machine learning prediction; and
setting, for each of the plurality of subjects, a value of each of the hybrid variables in the dataset at least in part by:
processing, using a machine learning model trained to predict a value of the hybrid variable, clinical record data associated with the subject to obtain a predicted hybrid variable value and an associated confidence score;
determining, using the confidence score associated with the predicted hybrid variable value, whether to set the value of the hybrid variable for the subject to the predicted hybrid variable value;
in response to determining to set the value of the hybrid variable for the subject to the predicted hybrid variable value:
setting the value of the hybrid variable for the subject to the predicted hybrid variable value in the dataset; and
in response to determining to not set the value of the hybrid variable for the subject to the predicted hybrid variable value:
obtaining input indicating a manually extracted hybrid variable value for the subject; and
setting the value of the hybrid variable for the subject to the manually extracted hybrid variable value in the dataset; and
setting, for each of the plurality of subjects, values of the non-hybrid variables to manually extracted values of the non-hybrid variables without obtaining machine learning predicted values of the non-hybrid variables.

2. The method of claim 1, wherein obtaining the input indicating the manually extracted hybrid variable value for the subject comprises:
generating a request for the manually extracted hybrid variable value for the subject; and
receiving, in response to the request, the input indicating the manually extracted hybrid variable value for the subject.

3. The method of claim 1, wherein the clinical record data comprises unstructured textual data, and processing, using the machine learning model trained to predict the value of the hybrid variable, the clinical record data associated with the subject to obtain the predicted hybrid variable value and the associated confidence score comprises:
identifying at least one portion of the unstructured textual data associated with the hybrid variable;
generating, using the at least one portion of the unstructured textual data associated with the hybrid variable, at least one set of features; and
providing the at least one set of features as input to the machine learning model to obtain an output indicating the predicted hybrid variable value and the confidence score associated with the predicted hybrid variable value.

4. The method of claim 1, wherein the machine learning model is trained to output probability values for each of multiple output classes, and the confidence score associated with the predicted hybrid variable value is a probability value output for a respective one of the multiple output classes output by the machine learning model as the predicted hybrid variable value.

5. The method of claim 1, wherein determining, using the confidence score associated with the predicted hybrid variable value, whether to set the value of the hybrid variable value for the subject to the predicted hybrid variable value comprises:
determining whether the confidence score associated with the predicted hybrid variable value meets a threshold confidence score;
determining to set the value of the hybrid variable for the first subject to the predicted hybrid variable value when it is determined that the confidence score associated with the predicted hybrid variable value meets the threshold confidence score; and
determining to not set the value of the hybrid variable for the first subject to the predicted hybrid variable value when it is determined that the confidence score associated with the predicted hybrid variable value does not meet the threshold confidence score.

6. The method of claim 5, wherein a threshold confidence score for a first hybrid variable of the plurality of hybrid variables is determined by:
identifying a plurality of candidate threshold confidence scores;
for each one of the plurality of candidate threshold confidence scores:
processing clinical record data associated with a set of subjects using a first machine learning model to obtain a set of predicted values of the first hybrid variable and a corresponding set of confidence scores;
determining values of the first hybrid variable for the set of subjects using the candidate threshold confidence score;
determining a measure of quality for the candidate threshold confidence score using the values of the first hybrid variable determined for the set of subjects; and
selecting the threshold confidence score from the plurality of candidate threshold confidence scores based on measures of quality determined for the plurality of candidate threshold scores.

7. The method of claim 1, wherein the plurality of hybrid variables includes a stage of cancer.

8. The method of claim 1, wherein the plurality of hybrid variables includes a metastatic cancer diagnosis.

9. The method of claim 1, wherein the plurality of hybrid variables includes a date of metastatic cancer diagnosis.

10. The method of claim 1, wherein setting, for each of the plurality of subjects, values of the non-hybrid variables to manually extracted values of the non-hybrid variables without obtaining machine learning predicted values of the non-hybrid variables comprises:
generating a GUI comprising an interface through which a user can input values of the non-hybrid variables; and
for each of the non-hybrid variables:
obtaining, through the GUI, input indicating a manually extracted non-hybrid variable value for the subject; and
setting the value of the non-hybrid variable for the subject to the manually extracted non-hybrid variable value.

11. The method of claim 1, wherein obtaining the input indicating the manually extracted hybrid variable value for the subject comprises:
generating a GUI displaying at least some of the clinical record data associated with the subject, the GUI including an interface through which a user can input a manually extracted value of the hybrid variable; and
receiving, through the GUI, the manually extracted hybrid variable value for the subject.

12. A system for using machine learning to automatically extract values of clinical variables for a plurality of subjects from clinical record data, the system comprising:
at least one processor; and
at least one non-transitory computer-readable storage medium storing instructions that, when executed by the at least one processor, cause the at least one processor to perform:
obtaining clinical record data associated with the plurality of subjects;
generating, using the clinical record, a dataset for storing values of a plurality of clinical variables, the plurality of clinical variables comprising:
a subset of clinical variables designated as hybrid variables that can have their values assigned by machine learning model prediction or by manual extraction; and
a subset of clinical variables designated as non-hybrid variables that cannot have their values assigned by machine learning prediction; and
setting, for each of the plurality of subjects, a value of each of the hybrid variables in the dataset at least in part by:
processing, using a machine learning model trained to predict a value of the hybrid variable, clinical record data associated with the subject to obtain a predicted hybrid variable value and an associated confidence score;
determining, using the confidence score associated with the predicted hybrid variable value, whether to set a value of the hybrid variable for the subject to the predicted hybrid variable value;
in response to determining to set the value of the hybrid variable for the subject to the predicted hybrid variable value:
setting the value of the hybrid variable for the subject to the predicted hybrid variable value in the dataset; and
in response to determining to not set the value of the hybrid variable for the subject to the predicted hybrid variable value:
obtaining input indicating a manually extracted hybrid variable value for the subject; and
setting the value of the hybrid variable for the subject to the manually extracted hybrid variable value in the dataset; and setting, for each of the plurality of subjects, values of the non-hybrid variables to manually extracted values of the non-hybrid variables without obtaining machine learning predicted values of the non-hybrid variables.

13. The system of claim 12, wherein obtaining the input indicating the manually extracted hybrid variable value for the subject comprises:
generating a request for the manually extracted hybrid variable value for the subject; and
receiving, in response to the request, the input indicating the manually extracted hybrid variable value for the subject.

14. The system of claim 12, wherein the clinical record data comprises unstructured textual data, and processing, using the machine learning model trained to predict the value of the hybrid variable, the clinical record data associated with the subject to obtain the predicted hybrid variable value and the associated confidence score comprises:
identifying at least one portion of the unstructured textual data associated with the hybrid variable;
generating, using the at least one portion of the unstructured textual data associated with the hybrid variable, at least one set of features; and
providing the at least one set of features as input to the machine learning model to obtain an output indicating the predicted hybrid variable value and the confidence score associated with the predicted hybrid variable value.

15. The system of claim 12, wherein the machine learning model is trained to output probability values for each of multiple output classes, and the confidence score associated with the predicted hybrid variable value is a probability value output for a respective one of the multiple output classes output by the machine learning model as the predicted hybrid variable value.

16. The system of claim 12, wherein determining, using the confidence score associated with the predicted hybrid variable value, whether to set the value of the hybrid variable for the subject to the predicted hybrid variable value comprises:
determining whether the confidence score associated with the predicted hybrid variable value meets a threshold confidence score;
determining to set the value of the hybrid variable for the subject to the predicted hybrid variable value when it is determined that the confidence score associated with the predicted hybrid variable value meets the threshold confidence score; and
determining to not set the value of the hybrid variable for the subject to the predicted hybrid variable value when it is determined that the confidence score associated with the predicted hybrid variable value does not meet the threshold confidence score.

17. The system of claim 12, wherein setting, for each of the plurality of subjects, values of the non-hybrid variables to manually extracted values of the non-hybrid variables without obtaining machine learning predicted values of the non-hybrid variables comprises:
generating a GUI comprising an interface through which a user can input values of the non-hybrid variables; and
for each of the non-hybrid variables:
obtaining, through the GUI, input indicating a manually extracted non-hybrid variable value for the subject; and
setting the value of the non-hybrid variable for the subject to the manually extracted non-hybrid variable value.

18. At least one non-transitory computer-readable storage medium storing instructions that, when executed by at least one processor, cause the at least one processor to perform a method of using machine learning to automatically extract values of clinical variables for a plurality of subjects from clinical record data, the method comprising:
- obtaining clinical record data associated with the plurality of subjects;
- generating, using the clinical record, a dataset for storing values of a plurality of clinical variables, the plurality of clinical variables comprising:
  - a subset of clinical variables designated as hybrid variables that can have their values assigned by machine learning model prediction or by manual extraction; and
  - a subset of clinical variables designated as non-hybrid variables that cannot have their values assigned by machine learning prediction; and
- setting, for each of the plurality of subjects, a value of each of the hybrid variables in the dataset at least in part by:
  - processing, using a machine learning model trained to predict a value of the hybrid variable, clinical record data associated with the subject to obtain a predicted hybrid variable value and an associated confidence score;
  - determining, using the confidence score associated with the predicted hybrid variable value, whether to set a value of the hybrid variable for the subject to the predicted hybrid variable value;
  - in response to determining to set the value of the hybrid variable for the subject to the predicted hybrid variable value:
    - setting the value of the hybrid variable for the subject to the predicted hybrid variable value in the dataset; and
  - in response to determining to not set the value of the hybrid variable for the subject to the predicted hybrid variable value:
    - obtaining input indicating a manually extracted hybrid variable value for the subject; and
    - setting the value of the hybrid variable for the subject to the manually extracted hybrid variable value in the dataset; and
- setting, for each of the plurality of subjects, values of the non-hybrid variables without obtaining machine learning predicted values of the non-hybrid variables.

19. The at least one non-transitory computer-readable storage medium of claim 18, wherein the machine learning model is trained to output probability values for each of multiple output classes, and the confidence score associated with the predicted hybrid variable value is a probability value output for a respective one of the multiple output classes output by the machine learning model as the predicted hybrid variable value.

20. The at least one non-transitory computer-readable storage medium of claim 18, wherein determining, using the confidence score associated with the predicted hybrid variable value, whether to set the value of the hybrid variable for the subject to the predicted hybrid variable value comprises:
- determining whether the confidence score associated with the predicted hybrid variable value meets a threshold confidence score;
- determining to set the value of the hybrid variable for the subject to the predicted hybrid variable value when it is determined that the confidence score associated with the predicted hybrid variable value meets the threshold confidence score; and
- determining to not set the value of the hybrid variable for the subject to the predicted hybrid variable value when it is determined that the confidence score associated with the predicted hybrid variable value does not meet the threshold confidence score.

* * * * *